US012799062B2

(12) United States Patent
Nandhikonda et al.

(10) Patent No.: US 12,799,062 B2
(45) Date of Patent: Nov. 17, 2026

(54) NON-IONIC SURFACTANTS AND METHODS OF MAKING AND USING THE SAME

(71) Applicant: Life Technologies Corporation, Carlsbad, CA (US)

(72) Inventors: Premchendar Nandhikonda, Rockford, IL (US); Schuyler B. Corry, Burlington, NC (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 19/429,573

(22) Filed: Dec. 22, 2025

(65) Prior Publication Data

US 2026/0184660 A1 Jul. 2, 2026

Related U.S. Application Data

(60) Provisional application No. 63/739,959, filed on Dec. 30, 2024.

(51) Int. Cl.

| | |
|---|---|
| ***C07C 47/575*** | (2006.01) |
| ***C07C 43/205*** | (2006.01) |
| ***C07C 43/23*** | (2006.01) |
| *C07C 309/66* | (2006.01) |

(52) U.S. Cl.

CPC ........ *C07C 47/575* (2013.01); *C07C 43/2055* (2013.01); *C07C 43/23* (2013.01); *C07C 309/66* (2013.01)

(58) Field of Classification Search

CPC .... C07C 47/575; C07C 43/2055; C07C 43/23

See application file for complete search history.

(56) References Cited

U.S. PATENT DOCUMENTS

| | | | |
|---|---|---|---|
| 8,343,268 | B2 | 1/2013 | Ma et al. |
| 9,556,217 | B2 | 1/2017 | Gellman et al. |
| 2003/0170617 | A1 | 9/2003 | Pasloske |
| 2024/0010590 | A1 | 1/2024 | Farcet et al. |

FOREIGN PATENT DOCUMENTS

| | | | |
|---|---|---|---|
| JP | H045265 | A | 1/1992 |
| JP | 2007332137 | A | 12/2007 |
| WO | WO 01/87253 | A1 | 11/2001 |
| WO | WO 2019/086463 | A1 | 5/2019 |

(Continued)

OTHER PUBLICATIONS

Joe, J.H., et al., A dendritic-linear block copolymer as a thermoresponsive non-ionic polymer, European Polymer Jornal, 118, 320-326 (Year: 2019).*

(Continued)

*Primary Examiner* — Yate' K Cutliff

(74) *Attorney, Agent, or Firm* — Klarquist Sparkman, LLP

(57) ABSTRACT

Disclosed herein are compounds that can be used as surfactants for various applications. The disclosed compounds are biodegradable and do not form toxic by-products when degraded. As such, the disclosed compounds can be used as replacements for current surfactants, such as current octylphenol ethoxylates (OPEs) and nonylphenol ethoxylates (NPEs) that have toxic effects when degraded. Also disclosed are methods of making and using the disclosed compounds.

16 Claims, 4 Drawing Sheets

(56) References Cited

FOREIGN PATENT DOCUMENTS

WO WO 2021/118900 A1 6/2021
WO WO 2022/029674 A1 2/2022

OTHER PUBLICATIONS

Omokawa, Y., et al., Effect of the incorporation of Glycolipid Analogues into the vesicle membrane composed of nonionic surfactant Span80 on the vesicle characteristics, Department of Materials Science and Biotechnology, Ehime University, Membrane, 32(5), 302-310 (Year: 2007).*

Zumpano, R., et al., Sodium Lauryl ether sulfates, pivotal surfactants for formulations: Rationalization of their assembly properties, Colloids and Surfaces A: Physcochemical and Engineering Aspects, 686, 133375 (Year: 2024).*

PubChem, Trimebutine, Springer Nature, SID 341180845 deposit 2017, 6 pages (Year: 2017).*

Bhadani et al., "Sustainable oleic and stearic acid based biodegradable surfactants," *RSC Adv.*, Feb. 2, 2017, 7, 10433.

Carter et al., "Nonionic Surfactants Promote the Incorporation of Silicone-Acrylic Hybrid Monomers in Emulsion Polymerization," *ACS Appl. Polym. Mater.* 4, pp. 4829-4838, 2022.

Chrusciel et al., "Interfacial Activity of 2-Ethylhexan-1-ol-Based Surfactants in Quasi-ternary Systems," *Journal Surfact. Deterg.*, 20:83-101, Oct. 17, 2016.

Farcet et al., "Development of a Triton X-100 replacement for effective virus inactivation in biotechnology processes," *Engineering Reports*, pp. 1-10, Nov. 22, 2019.

Farcet et al., "Synthesis of "Nereid," a new phenol-free detergent to replace Triton X-100 in virus inactivation," *J. Med Virol.* 93:3880-3889, Nov. 28, 2020.

Gooran et al., "Supported Lipid Bilayer Platform for Characterizing the Membrane-Disruptive Behaviors of Triton X-100 and Potential Detergent Replacements," *International Journal of Molecular Sciences*, 23, 869, Jan. 14, 2022.

Hunter et al., "Identification of compendial nonionic detergents for the replacement of Triton X-100 in bioprocessing," *Biotechnology Progress*, pp., 1-9, Jan. 11, 2022.

Koley and Bard, Triton X-100 concentration effects on membrane permeability of a single HeLa cell by scanning electrochemical microscopy (SECM), *PNAS*, vol. 107, No. 39, pp. 16783-16787, Sep. 28, 2010.

Liu et al., "Synthesis and Characterization of Furan-Based Non-Ionic Surfactants (fbnios)," *Langmuir*, vol. 39, pp. 8974-8983, Jun. 21, 2023.

Ontiveros et al., "Design and Properties of a Novel Family of Nonionic Biobased Furanic Hydroxyester and Amide Surfactants," *ACS Sustainable Chemistry & Engineering*, 9, 16977-16988, 2021.

Ortiz et al., "Surfactants produced from carbohydrate derivatives: A review of the biobased building blocks used in their synthesis," *Journal Surfact. Deterg.*, 25: 147-183, Dec 26, 2021.

Shehzad et al., "Magnetic surfactants: A review of recent progress in synthesis and applications," *Advances in Colloid and Interface Science*, 293, 102441, May 19, 2021.

Velty et al., "Synthetic Routes for Designing Furanic and Non Furanic Biobased Surfactants from 5-Hydroxymethylfurfural," *ChemSusChem*, 15, e202200181, 2022.

Vicente et al., "Impact of Surface Active Ionic Liquids on the Cloud Points of Nonionic Surfactants and the Formation of Aqueous Micellar Two-Phase Systems," *Journal of Physical Chemistry*, 121, pp. 8742-8755, Aug. 23, 2017.

Gracida et al., "Synthesis of Anionic Surfactant and Their Application in Washing of Oil-Contaminated Soil," *Journal of Surfactants and Detergents: JSD; A Journal of the American Oil Chemists Society*, vol. 20, No. 2, pp. 493-502, Jan. 31, 2017.

International Search Report and Written Opinion issued in International Application No. PCT/US2025/060970, mailed May 21, 2026, 16 pages.

Omokawa et al., "Effect of the Incorporation of Glycolipid Analogues into the Vesicle Membrane Composed of Nonionic Surfactant Span80 on the Vesicle Characteristics," *Membrane*, vol. 32, No. 5, pp. 302-310, Jan. 1, 2007.

Percec et al., "Self-Assembly of Janus Dendrimers into Uniform Dendrimersomes and Other Complex Architectures," *Science*, vol. 328, No. 5981, pp. 1009-1014, May 21, 2010.

* cited by examiner

NON-IONIC SURFACTANTS AND METHODS OF MAKING AND USING THE SAME

CROSS REFERENCE TO RELATED APPLICATIONS

This application claims the benefit of priority under 35 U.S.C. § 119 (e) to U.S. Provisional Application No. 63/739, 959 filed on Dec. 30, 2024, the contents of which are hereby expressly incorporated herein by reference in their entirety as though fully set forth herein.

FIELD

The present disclosure is directed to new biodegradable surfactants and methods of making and using the same.

BACKGROUND

Currently available non-ionic surfactants, such as Triton™ X-100 and Tergitol™ NP-40, are part of a group of chemicals known as octylphenol ethoxylates (OPEs) and nonylphenol ethoxylates (NPEs) that, when broken down in the environment, have toxic effects on aquatic organisms at extremely low concentrations. OPEs and NPEs are toxic xenobiotic compounds classified as endocrine disrupters capable of interfering with the hormonal system of numerous organisms. The use of OPEs and NPEs has already been banned for most uses in the EEA, UK, and Switzerland requiring capture, diversion, and incineration of all waste with limited exemptions or authorization. Many other countries are evaluating similar actions where exemptions or authorizations are less clear than in the EU. There exists a need in the art for new surfactants that are biodegradable and do not exhibit the toxic effects associated with currently available non-ionic surfactants.

SUMMARY

Disclosed herein is a compound having a structure according to Formula I,

Formula I

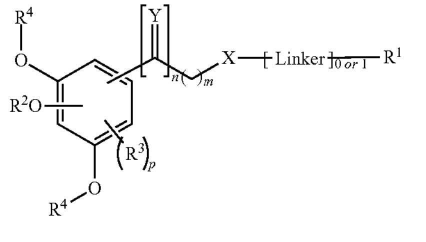

wherein:

$R^1$ is a hydrophilic group;

$R^2$ is a lipophilic group;

X is selected from oxygen, sulfur, or $N(R^5)$;

$R^3$ is selected from heteroaliphatic, aliphatic, or aryl;

each $R^4$ independently is aliphatic;

Y is selected from oxygen, sulfur, or $N(R^5)$;

the linker, when present, is aliphatic or has a formula —C(═Z)—W—C(═Z)—X', wherein each Z independently is oxygen, sulfur, or $NR^5$, W is an aliphatic or heteroaliphatic group, and X'O is oxygen, sulfur, or $NR^5$;

n is an integer selected from 0 or 1;

m is an integer selected from 0 to 6, provided that, if n is 0, then m is 1;

p is an integer selected from 0 to 2; and each $R^5$ group independently is selected from hydrogen, aliphatic, aromatic, or heteroaliphatic.

Also disclosed is a method, comprising exposing a sample to a compound according to the present disclosure. Also disclosed is a method of lysing a cell, comprising contacting the cell with an amount of a compound according to the present disclosure sufficient to facilitate cell lysis.

Also disclosed is a composition, comprising a compound according to the present disclosure. Also disclosed is a kit, comprising a compound according to the present disclosure; and a container.

The foregoing and other objects, features, and advantages of the present disclosure will become more apparent from the following detailed description, which proceeds with reference to the accompanying figures.

BRIEF DESCRIPTION OF THE DRAWINGS

FIGS. 1A and 1B are graphs showing results from using a compound according to the present disclosure (namely, Compound 1 (SY-2)) as a surfactant in cell lysing, wherein FIG. 1A shows a graph of results from a bicinchoninic acid (BCA) assay, wherein protein recovery was assessed for Compound 1 (SY-2), at various concentrations, as compared to the conventional non-ionic surfactants NP40 and EH9; and FIG. 1B shows is a graph illustrating the background signal from a mixture containing only the disclosed compound, buffer and a fluorescent dye, that is without a protein sample or cell lysate present.

DETAILED DESCRIPTION

Overview of Terms

Figure 1A:
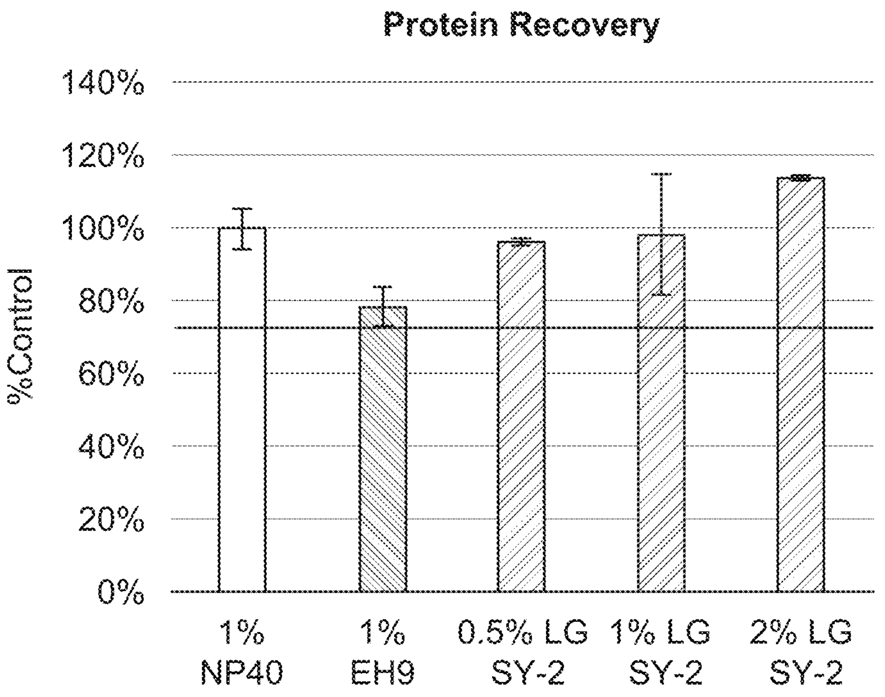

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements unless the context clearly indicates otherwise.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Although the steps of some of the disclosed methods are described in a particular, sequential order for convenient presentation, it should be understood that this manner of description encompasses rearrangement, unless a particular ordering is required by specific language set forth below. For example, steps described sequentially may in some cases be rearranged or performed concurrently. Additionally, the description sometimes uses terms like "produce" or "provide" to describe the disclosed methods. These terms are high-level abstractions of the actual steps that are performed. The actual steps that correspond to these terms will vary depending on the particular implementation and are readily discernible by one of ordinary skill in the art.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods and in some aspects encompasses a range up to ±15% of that numerical value, unless the context clearly dictates otherwise.

Certain functional group terms used herein include a symbol "-", which is used to show how the defined functional group attaches to, or within, the compound to which it is bound. Also, a dashed bond (i.e., "---") as used in certain formulas described herein indicates an "optional" bond to a substituent or atom of the formula other than hydrogen in the sense that the bond (and in some embodiments, the substituent) may or may not be present. In any formulas comprising a dashed bond, if the optional bond and/or any corresponding substituent is not present, then the valency requirements of any atom(s) bound thereto is completed by a bond to a hydrogen atom.

The symbol "~" is used to indicate a bond disconnection in abbreviated structures/formulas provided herein. A person of ordinary skill in the art recognizes that the definitions provided below and the compounds and formulas included herein are not intended to include impermissible substitution patterns (e.g., methyl substituted with 5 different groups, and the like). Such impermissible substitution patterns are easily recognized by a person of ordinary skill in the art. In formulas and compounds disclosed herein, a hydrogen atom is present and completes any formal valency requirements (but may not necessarily be illustrated) wherever a functional group or other atom is not illustrated. For example, a phenyl ring that is drawn as

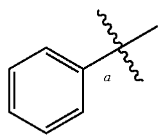 [SMILES: *c1ccccc1]

comprises a hydrogen atom attached to each carbon atom of the phenyl ring other than the "a" carbon, even though such hydrogen atoms are not illustrated. Any functional group disclosed herein and/or defined above can be substituted or unsubstituted, unless otherwise indicated herein.

If a group R is depicted as "floating" on a ring system, as for example in the group:

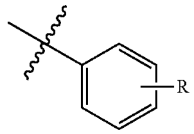

then, unless otherwise defined, a substituent R can reside on any atom of the fused bicyclic ring system, excluding the atom carrying the bond with the "~" symbol, so long as a stable structure is formed. In the example depicted, the R group can reside on an atom in either the left side or the right side ring of the naphthylene ring system.

When there are more than one such depicted "floating" groups, as for example in the formula:

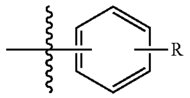

where there are two groups, namely, the R and the bond indicating attachment to a parent structure; then, unless otherwise defined, the "floating" groups can reside on any atoms of the ring system, again assuming each replaces a depicted, implied, or expressly defined hydrogen on the ring system and a chemically stable compound would be formed by such an arrangement.

To facilitate review of the disclosure, the following explanations of specific terms are provided.

Aldehyde:—C(O) H.

Aliphatic: A hydrocarbon group having at least one carbon atom to 50 carbon atoms ($C_{1-50}$), such as one to 25 carbon atoms ($C_{1-25}$), or one to ten carbon atoms ($C_{1-10}$), and which includes alkanes (or alkyl), alkenes (or alkenyl), alkynes (or alkynyl), including cyclic versions thereof, and further including straight- and branched-chain arrangements, and all stereo and position isomers as well. Aliphatic groups may be substituted with one or more groups other than hydrogen, such as aliphatic, heteroaliphatic, haloaliphatic, haloheteroaliphatic, aromatic, or an organic functional group.

Alkenyl: An unsaturated monovalent hydrocarbon having at least two carbon atoms to 50 carbon atoms ($C_{2-50}$), such as two to 25 carbon atoms ($C_{2-25}$), or two to ten carbon atoms ($C_{2-10}$), and at least one carbon-carbon double bond, wherein the unsaturated monovalent hydrocarbon can be derived from removing one hydrogen atom from one carbon atom of a parent alkene. An alkenyl group can be branched, straight-chain, cyclic, cis, or trans (e.g., E or Z).

Alkoxy: —O-aliphatic, such as —O-alkyl, —O-alkenyl, —O-alkynyl; with exemplary embodiments including, but not limited to, methoxy, ethoxy, n-propoxy, isopropoxy, n-butoxy, t-butoxy, sec-butoxy, n-pentoxy (wherein any of the aliphatic components of such groups can comprise no double or triple bonds, or can comprise one or more double and/or triple bonds). Alkoxy groups may be substituted with one or more groups other than hydrogen, such as aliphatic, heteroaliphatic, haloaliphatic, haloheteroaliphatic, aromatic, or an organic functional group.

Alkyl: A saturated monovalent hydrocarbon having at least one carbon atom to 50 carbon atoms ($C_{1-50}$), such as one to 25 carbon atoms ($C_{1-25}$), or one to ten carbon atoms ($C_{1-10}$), wherein the saturated monovalent hydrocarbon can be derived from removing one hydrogen atom from one carbon atom of a parent compound (e.g., alkane). An alkyl group can be branched, straight-chain, or cyclic.

Alkynyl: An unsaturated monovalent hydrocarbon having at least two carbon atoms to 50 carbon atoms ($C_{2-50}$), such as two to 25 carbon atoms ($C_{2-25}$), or two to ten carbon atoms ($C_{2-10}$), and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic.

Amide:—C(O)NR$^b$R$^c$ or —NR$^b$C(O)R$^c$ wherein each of R$^b$ and R$^c$ independently is selected from hydrogen, aliphatic, heteroaliphatic, haloaliphatic, haloheteroaliphatic, aromatic, or an organic functional group and can be substituted with one or more groups other than hydrogen, such as aliphatic, heteroaliphatic, haloaliphatic, haloheteroaliphatic, aromatic, or an organic functional group.

Amino: —NR$^b$R$^c$, wherein each of R$^b$ and R$^c$ independently is selected from hydrogen, aliphatic, heteroaliphatic, haloaliphatic, haloheteroaliphatic, aromatic, or an organic functional group, and can be substituted with one or more groups other than hydrogen, such as aliphatic, heteroaliphatic, haloaliphatic, haloheteroaliphatic, aromatic, or an organic functional group.

Aromatic: A cyclic, conjugated group or moiety of, unless specified otherwise, from 5 to 15 ring atoms having a single ring (e.g., phenyl) or multiple condensed rings in which at least one ring is aromatic (e.g., naphthyl, indolyl, or pyrazolopyridinyl); that is, at least one ring, and optionally multiple condensed rings, have a continuous, delocalized π-electron system. Typically, the number of out of plane TT-electrons corresponds to the Hückel rule (4n+2). The point of attachment to the parent structure typically is through an aromatic portion of the condensed ring system. For example,

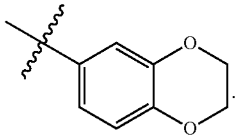 [SMILES: *c1ccc2c(c1)OCCO2]

However, in certain examples, context or express disclosure may indicate that the point of attachment is through a non-aromatic portion of the condensed ring system. For example,

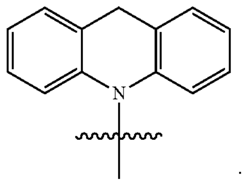 [SMILES: *N1c2ccccc2Cc2ccccc21]

An aromatic group or moiety may comprise only carbon atoms in the ring, such as in an aryl group or moiety, or it may comprise one or more ring carbon atoms and one or more ring heteroatoms comprising a lone pair of electrons (e.g. S, O, N, P, or Si), such as in a heteroaryl group or moiety. Aromatic groups may be substituted with one or more groups other than hydrogen, such as aliphatic, heteroaliphatic, haloaliphatic, haloheteroaliphatic, aromatic, or an organic functional group.

Aroxy: —O-aromatic. Aroxy groups may be substituted with one or more groups other than hydrogen, such as aliphatic, heteroaliphatic, haloaliphatic, haloheteroaliphatic, aromatic, or an organic functional group.

Aryl: An aromatic carbocyclic group comprising at least five carbon atoms to 15 carbon atoms ($C_{5-15}$), such as five to ten carbon atoms ($C_{5-10}$), having a single ring or multiple condensed rings, which condensed rings can or may not be aromatic provided that the point of attachment to a remaining position of the compounds disclosed herein is through an atom of the aromatic carbocyclic group. Aryl groups may be substituted with one or more groups other than hydrogen, such as an aliphatic, heteroaliphatic, haloaliphatic, haloheteroaliphatic, aromatic, or an organic functional group.

Azo: —N═NR$^a$ wherein R$^a$ is hydrogen, aliphatic, heteroaliphatic, haloaliphatic, haloheteroaliphatic, aromatic, or an organic functional group. Azo groups may be substituted with one or more groups other than hydrogen, such as aliphatic, heteroaliphatic, haloaliphatic, haloheteroaliphatic, aromatic, or an organic functional group.

Carbamate: —OC(O)NR$^b$R$^c$, wherein each of R$^b$ and R$^c$ independently is selected from hydrogen, aliphatic, heteroaliphatic, haloaliphatic, haloheteroaliphatic, aromatic, or an organic functional group. Carbamate groups can be substituted with one or more groups other than hydrogen, such as aliphatic, heteroaliphatic, haloaliphatic, haloheteroaliphatic, aromatic, or an organic functional group.

Carbonate: —OC(O)OR$^a$, wherein R$^a$ is selected from aliphatic, heteroaliphatic, haloaliphatic, haloheteroaliphatic, aromatic, or an organic functional group. Carbonate groups can be substituted with one or more groups other than hydrogen, such as aliphatic, heteroaliphatic, haloaliphatic, haloheteroaliphatic, aromatic, or an organic functional group. In independent embodiments, R$^a$ can be hydrogen.

Carboxyl:—C(O)OH.

Carboxylate:—C(O)O$^-$ or salts thereof, wherein the negative charge of the carboxylate group may be balanced with an M$^+$ counterion, wherein M$^+$ may be an alkali ion, such as K$^+$, Na$^+$, Li$^+$; an ammonium ion, such as $^+$N(R$^b$)$_4$ where R$^b$ is H, aliphatic, heteroaliphatic, haloaliphatic, haloheteroaliphatic, or aromatic; or an alkaline earth ion, such as $[Ca^{2+}]_{0.5}$, $[Mg^{2+}]_{0.5}$, or $[Ba^{2+}]_{0.5}$.

Cyano: —CN.

Degree of Polymerization: The number of monomer units in a polymer. In the context of the present disclosure, when discussing, for example, polyalkene oxide and/or polyalkylene amine polymers comprising repeat units of monomers, the degree of polymerization is typically defined by a mass average molecular weight.

Disulfide: —SSR$^a$, wherein R$^a$ is selected from hydrogen, aliphatic, heteroaliphatic, haloaliphatic, haloheteroaliphatic, aromatic, or an organic functional group. Disulfide groups can be substituted with one or more groups other than hydrogen, such as aliphatic, heteroaliphatic, haloaliphatic, haloheteroaliphatic, aromatic, or an organic functional group.

Dithiocarboxylic:—C(S)SR$^a$ wherein R$^a$ is selected from hydrogen, aliphatic, heteroaliphatic, haloaliphatic, haloheteroaliphatic, aromatic, or an organic functional group. Dithiocarboxylic groups can be substituted with one or more groups other than hydrogen, such as aliphatic, heteroaliphatic, haloaliphatic, haloheteroaliphatic, aromatic, or an organic functional group.

Ester:—C(O)OR$^a$ or —OC(O)R$^a$, wherein R$^a$ is selected from aliphatic, heteroaliphatic, haloaliphatic, haloheteroaliphatic, aromatic, or an organic functional group. Ester groups can be substituted with one or more groups other than hydrogen, such as aliphatic, heteroaliphatic, haloaliphatic, haloheteroaliphatic, aromatic, or an organic functional group.

Ether: -aliphatic-O-aliphatic, -aliphatic-O-aromatic, -aromatic-O-aliphatic, or -aromatic-O-aromatic, including any polymers thereof having repeats of any such groups (e.g., polyalkene oxide compounds). Ether groups can be substituted with one or more groups other than hydrogen, such as aliphatic, heteroaliphatic, haloaliphatic, haloheteroaliphatic, aromatic, or an organic functional group.

Halo (or halide or halogen): Fluoro, chloro, bromo, or iodo. In some embodiments, halo can also include astatine.

Haloaliphatic: An aliphatic group wherein one or more hydrogen atoms, such as one to 10 hydrogen atoms, independently is replaced with a halogen atom, such as fluoro, bromo, chloro, or iodo. Haloaliphatic groups can be substituted with one or more groups other than hydrogen, such as aliphatic, heteroaliphatic, haloaliphatic, haloheteroaliphatic, aromatic, or an organic functional group.

Haloheteroaliphatic: A heteroaliphatic group wherein one or more hydrogen atoms, such as one to 10 hydrogen atoms, independently is replaced with a halogen atom, such as fluoro, bromo, chloro, or iodo. Haloheteroaliphatic groups can be substituted with one or more groups other than hydrogen, such as aliphatic, heteroaliphatic, haloaliphatic, haloheteroaliphatic, aromatic, or an organic functional group.

Heteroatom: An atom other than carbon or hydrogen, such as (but not limited to) oxygen, nitrogen, sulfur, silicon, boron, selenium, or phosphorous. A heteroatom does not include a halogen atom.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, silicon, boron, selenium, phosphorous, and oxidized forms thereof within the group. Alkoxy, ether, amino (excluding $NH_2$), disulfide (wherein R$^a$ is other than H), peroxy (wherein R$^a$ is other than H), and thioether groups are exemplary (but non-limiting) examples of heteroaliphatic. Heteroaliphatic groups can be substituted with one or more groups other than hydrogen, such as aliphatic, heteroaliphatic, haloaliphatic, haloheteroaliphatic, aromatic, or an organic functional group.

Hydrophilic: A hydrophilic group according to the present disclosure is a functional group or other chemical group that exhibits affinity for water. In some aspects, a hydrophilic group can further comprise a lipophilic portion; however, in such instances, the hydrophilic group is predominately hydrophilic and the lipophilic portion makes up a minor (e.g., less than 50%) of the hydrophilic group. Solely by way of example, a hydrophilic group can comprise a combination of a heteroaliphatic group and an aliphatic group and still be hydrophilic because the heteroaliphatic group makes up a greater proportion of the molecular weight of the total hydrophilic group than does the aliphatic group.

Hydrophilic-Lipophilic Balance (HLB): A numerical value that represents the balance of the size and strength of the hydrophilic and lipophilic moieties of a surfactant compound. The HLB scale ranges from 0 to 20.

Hydroxyl: —OH

Ketone:—C(O)R$^a$, wherein R$^a$ is selected from aliphatic, heteroaliphatic, haloaliphatic, haloheteroaliphatic, aromatic, or an organic functional group. Ketone groups can be substituted with one or more groups other than hydrogen, such as aliphatic, heteroaliphatic, haloaliphatic, haloheteroaliphatic, aromatic, or an organic functional group.

Lipophilic: A lipophilic group according to the present disclosure is a functional group or other chemical group that lacks affinity for water.

Tergitol™ NP-40: A compound having a structure

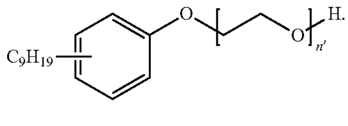

Organic Functional Group: A functional group that may be provided by any combination of aliphatic, heteroaliphatic, aromatic, haloaliphatic, and/or haloheteroaliphatic groups, or that may be selected from, but not limited to, aldehyde; aroxy; acyl halide; halogen; nitro; cyano; azide; carboxyl (or carboxylate); amide; ketone; carbonate; imine; azo; carbamate; hydroxyl; thiol; sulfonyl (or sulfonate); oxime; ester; thiocyanate; thioketone; thiocarboxylic acid; thioester; dithiocarboxylic; phosphonate; phosphate; silyl ether; sulfinyl; sulfonamide; thial; or combinations thereof. Organic functional groups can be substituted with one or more groups other than hydrogen, such as aliphatic, heteroaliphatic, haloaliphatic, haloheteroaliphatic, aromatic, or an organic functional group.

Oxime: —CR$^a$═NOH, wherein R$^a$ is hydrogen, aliphatic, heteroaliphatic, haloaliphatic, haloheteroaliphatic, aromatic, or an organic functional group. Oxime groups can be substituted with one or more groups other than hydrogen, such as aliphatic, heteroaliphatic, haloaliphatic, haloheteroaliphatic, aromatic, or an organic functional group.

Peroxy: —O—OR$^a$ wherein R$^a$ is hydrogen, aliphatic, heteroaliphatic, haloaliphatic, haloheteroaliphatic, aromatic, or an organic functional group. Peroxy groups can be substituted with one or more groups other than hydrogen, such as aliphatic, heteroaliphatic, haloaliphatic, haloheteroaliphatic, aromatic, or an organic functional group.

Phosphate: —O—P(O)(OR$^a$) 2, wherein each R$^a$ independently is hydrogen, aliphatic, heteroaliphatic, haloaliphatic, haloheteroaliphatic, aromatic, or an organic functional group; or wherein one or more R$^a$ groups are not present and the phosphate group therefore has at least one negative charge, which can be balanced by a counterion, $M^+$, wherein each $M^+$ independently can be an alkali ion, such as $K^+$, $Na^+$, $Li^+$; an ammonium ion, such as $^+N(R^b)_4$ where R$^b$ is H, aliphatic, heteroaliphatic, haloaliphatic, haloheteroaliphatic, or aromatic; or an alkaline earth ion, such as $[Ca^{2+}]_{0.5}$, $[Mg^{2+}]_{0.5}$, or $[Ba^{2+}]_{0.5}$. The $R^a$ groups of the phosphate can be substituted with one or more groups other than hydrogen, such as aliphatic, heteroaliphatic, haloaliphatic, haloheteroaliphatic, aromatic, or an organic functional group.

Phosphonate: —$P(O)(OR^a)$ 2, wherein each $R^a$ independently is hydrogen, aliphatic, heteroaliphatic, haloaliphatic, haloheteroaliphatic, aromatic, or an organic functional group; or wherein one or more $R^a$ groups are not present and the phosphate group therefore has at least one negative charge, which can be balanced by a counterion, $M^+$, wherein each $M^+$ independently can be an alkali ion, such as $K^+$, $Na^+$, $Li^+$; an ammonium ion, such as $^+N(R^b)$ 4 where $R^b$ is H, aliphatic, heteroaliphatic, haloaliphatic, haloheteroaliphatic, or aromatic; or an alkaline earth ion, such as $[Ca^{2+}]_{0.5}$, $[Mg^{2+}]_{0.5}$, or $[Ba^{2+}]_{0.5}$. The $R^a$ groups of the phosphonate group can be substituted with one or more groups other than hydrogen, such as aliphatic, heteroaliphatic, haloaliphatic, haloheteroaliphatic, aromatic, or an organic functional group.

Silyl Ether: —$OSiR^aR^bR^c$, wherein each of $R^a$, $R^b$ and $R^c$ independently is selected from hydrogen, aliphatic, heteroaliphatic, haloaliphatic, haloheteroaliphatic, aromatic, or an organic functional group. Silyl ether groups can be substituted with one or more groups other than hydrogen, such as aliphatic, heteroaliphatic, haloaliphatic, haloheteroaliphatic, aromatic, or an organic functional group.

Sulfinyl: —$S(O)R^a$, wherein $R^a$ is selected from hydrogen, aliphatic, heteroaliphatic, haloaliphatic, haloheteroaliphatic, aromatic, or an organic functional group. Sulfinyl groups can be substituted with one or more groups other than hydrogen, such as aliphatic, heteroaliphatic, haloaliphatic, haloheteroaliphatic, aromatic, or an organic functional group.

Sulfonyl: —$SO_2R^a$, wherein $R^a$ is selected from hydrogen, aliphatic, heteroaliphatic, haloaliphatic, haloheteroaliphatic, aromatic, or an organic functional group. Sulfonyl groups can be substituted with one or more groups other than hydrogen, such as aliphatic, heteroaliphatic, haloaliphatic, haloheteroaliphatic, aromatic, or an organic functional group.

Sulfonamide: —$SO_2NR^bR^c$ or —$N(R^b)$ $SO_2R^c$, wherein each of $R^b$ and $R^c$ independently is selected from hydrogen, aliphatic, heteroaliphatic, haloaliphatic, haloheteroaliphatic, aromatic, or an organic functional group. Sulfonamide groups can be substituted with one or more groups other than hydrogen, such as aliphatic, heteroaliphatic, haloaliphatic, haloheteroaliphatic, aromatic, or an organic functional group.

Sulfonate: —$SO_3^-$, wherein the negative charge of the sulfonate group may be balanced with an $M^+$ counter ion, wherein $M^+$ may be an alkali ion, such as $K^+$, $Na^+$, $Li^+$; an ammonium ion, such as $^+N(R^b)$ 4 where $R^b$ is H, aliphatic, heteroaliphatic, haloaliphatic, haloheteroaliphatic, or aromatic; or an alkaline earth ion, such as $[Ca^{2+}]_{0.5}$, $[Mg^{2+}]_{0.5}$, or $[Ba^{2+}]_{0.5}$.

Surfactant: A compound that lowers surface tension between two fluids (liquids and/or gases) and/or between a solid and a fluid. Surfactants can exhibit properties the allow their use as surfactants, dispersants, emulsifiers, foaming agents, wetting agents, lubricants, or a combination thereof.

Terminating Group: A functional group that is used to terminate an $R^1$ group of the formulas according to the present disclosure.

Thial:—C(S)H.

Thiocarboxylic acid:—C(O)SH, or —C(S)OH.

Thiocyanate: —S—CN or —N=C=S.

Thioester:—$C(O)SR^a$ or —$C(S)OR^a$ wherein $R^a$ is selected from hydrogen, aliphatic, heteroaliphatic, haloaliphatic, haloheteroaliphatic, aromatic, or an organic functional group. Thioester groups can be substituted with one or more groups other than hydrogen, such as aliphatic, heteroaliphatic, haloaliphatic, haloheteroaliphatic, aromatic, or an organic functional group.

Thioether: —S-aliphatic or —S-aromatic, such as —S-alkyl, —S-alkenyl, —S-alkynyl, —S-aryl, or —S-heteroaryl; or -aliphatic-S-aliphatic, -aliphatic-S-aromatic, -aromatic-S-aliphatic, or -aromatic-S-aromatic. Thioether groups can be substituted with one or more groups other than hydrogen, such as aliphatic, heteroaliphatic, haloaliphatic, haloheteroaliphatic, aromatic, or an organic functional group.

Thioketone:—C(S) $R^a$ wherein $R^a$ is selected from hydrogen, aliphatic, heteroaliphatic, haloaliphatic, haloheteroaliphatic, aromatic, or an organic functional group. Thioketone groups can be substituted with one or more groups other than hydrogen, such as aliphatic, heteroaliphatic, haloaliphatic, haloheteroaliphatic, aromatic, or an organic functional group.

Triton™ X-100: A compound having a structure

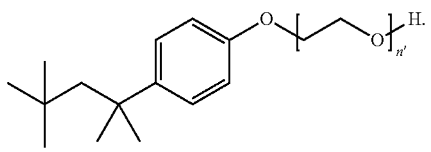

Introduction

Surfactants play an important role in life science technology and other various industries. With respect to their roles in the life sciences, they are often important components used in both nucleic acid purification and direct PCR processes. For example, in direct PCR, surfactants are needed to enhance the efficiency of the reaction by improving the accessibility of the DNA template. They also can be used to aid in cell lysis, viral inactivation, enhancing DNA accessibility, reducing non-specific binding, and ultimately contributing to the success of obtaining pure nucleic acids and amplifying specific DNA targets. Other processes and/or applications that rely on surfactants are discussed herein and can include, but are not limited to, DNA hybridization, kits for diagnosing allergy-, asthma-, and autoimmune-related diseases, nucleic acid-based sample preparation workflows, and the like.

Current non-ionic surfactants, such as Triton™ X-100, Tergitol™ NP-40, and/or EH9, that are available as surfactants for myriad biological and/or other industrial uses have a trade-off associated with good performance: they produce degradation by-products that exhibit endocrine disruption effects that interfere with the hormonal system of numerous organisms, particularly aquatic species. These surfactants are often used in sample preparation products, including protein extraction buffers, wash buffers, protein interaction kits, and protein purification kits. To date, no alternative surfactants are available as direct replacements for Triton™ X-100 and/or Tergitol™ NP-40, particularly those that are suitable for life science applications.

While less hazardous surfactants are available, they do not meet quality or performance standards across a broad range of products or applications, including sensitive biological assays typically used in life science technologies.

The present disclosure is directed to new compounds that can be used to replace current surfactants, like Triton™ X-100 and/or Tergitol™ NP-40. The disclosed compounds are less hazardous than Triton™ X-100 and/or Tergitol™ NP-40, but do not sacrifice performance as they work as effectively as, or better than, Triton™ X-100 and/or Tergitol™ NP-40. The disclosed compounds can be prepared using cost-effective methods and are biodegradable without producing toxic by-products like the endocrine disrupting by-products that are produced from degradation of Triton™ X-100 and/or Tergitol™ NP-40. The disclosed compounds are suitable for use as surfactants in myriad applications/industries.

Compounds

Disclosed herein are aspects of a compound that exhibits surfactant properties. In some aspects, the compounds of the present disclosure can have a structure according to Formula I.

Formula I

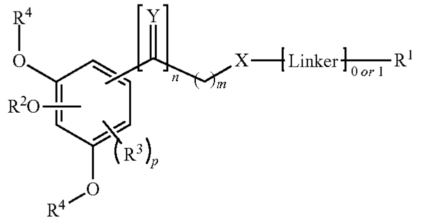

With reference to Formula I, $R^1$ is selected to be predominantly hydrophilic, such as comprising a heteroaliphatic group or a combination of a heteroaliphatic group and an aliphatic group; $R^2$ and each $R^4$ independently is a lipophilic group or a hydrophilic group, provided that if one of $R^2$ or (one or more) $R^4$ is a hydrophilic group, then $R^1$ and the other of $R^2$ or (either) $R^4$ is selected to provide the compound with a hydrophilic-lipophilic balance ("HLB") (calculated using Griffin's Method) value ranging from 10 to 18 (or, if both $R^2$ and one or more $R^4$ are hydrophilic groups, then $R^1$ is selected to provide the compound with such an HLB value); X is selected from oxygen, sulfur, or $N(R^5)$; $R^3$ is selected from heteroaliphatic, aliphatic, or aryl; each $R^4$ independently is aliphatic; Y is selected from oxygen, sulfur, or $N(R^5)$; the linker, when present (as indicated with subscript "1" in Formula I), is aliphatic or has a formula $-C(=Z)-W-C(=Z)-X'$, wherein each Z independently is oxygen, sulfur, or $NR^5$, W is an aliphatic or heteroaliphatic group (e.g., a N-containing heteroaliphatic group, an O-containing heteroaliphatic group, or an S-containing heteroaliphatic group), and X'O is oxygen, sulfur, or $N(R^5)$; n is an integer selected from 0 or 1; m is an integer selected from 0 to 6, such as 0, 1, 2, 3, 4, 5, or 6, provided that if n is 0, then m is 1; and p is an integer selected from 0 to 2, such as 0, 1, or 2. With reference to $R^5$ groups disclosed above, each $R^5$ group independently is selected from hydrogen, aliphatic, aromatic, or heteroaliphatic.

In any of the aspects in the present disclosure, the hydrophilic and lipophilic groups for $R^1$, $R^2$, and/or (one or both of) $R^4$ are selected to provide a hydrophilic-lipophilic balance ("HLB") value ranging from 10 to 18, such as 10 to 12, or 10 to 13, or 11 to 13, or 11 to 14, or 12 to 14, or 12 to 15, or 13 to 15, or 13 to 16, or 14 to 16, or 11 to 18, or 12 to 18, or 13 to 18, or 14 to 18, or 15 to 18, or 16 to 18, or 17 to 18.

In some aspects, $R^1$ comprises a heteroaliphatic group, such as a linear heteroaliphatic group or a cyclic heteroaliphatic group (e.g., a five-membered or 6-membered heterocyclic group). In some aspects, $R^1$ can include an aliphatic group in combination with the heteroaliphatic group. In some aspects, $R^1$ is a polyalkylene oxide group (e.g., a polyethylene glycol (PEG), a polypropylene glycol, or a combination thereof), a polyalkylene amine group (e.g., a polyethylene amine (PEI), a polypropylene amine, or a combination thereof), or comprises a cyclic $C_{4-5}$heteroaliphatic group, such as a sugar molecule. In some aspects, $R^1$ comprises a combination of (i) a polyalkylene oxide group or a polyalkylene amine group or a cyclic $C_{4-5}$heteroaliphatic group, and (ii) an aliphatic group. In aspects comprising an $R^1$ group that is a polyalkylene oxide or a polyalkylene amine, the polyalkylene oxide/amine can be terminated with a hydrogen atom or a terminating group, wherein the terminating group can be an aliphatic group, an aromatic group, or the like. In particular aspects, $R^1$ is a PEG or PEI group having a mass average molecular weight ranging from 500 g/mol to 800 g/mol, such as 525 g/mol to 800 g/mol, or 550 g/mol to 800 g/mol, or 575 g/mol to 800 g/mol, or 600 g/mol to 800 g/mol, or 625 g/mol to 800 g/mol, or 650 g/mol to 800 g/mol, or 675 g/mol to 800 g/mol, or 700 g/mol to 800 g/mol, or 725 g/mol to 800 g/mol, or 750 g/mol to 800 g/mol, or 775 g/mol to 800 g/mol. In particular aspects, the PEG group has a mass average molecular weight ranging from 525 g/mol to 575 g/mol, or 725 g/mol to 775 g/mol. In representative aspects, the PEG group has a mass average molecular weight of 550 g/mol or 750 g/mol. In any such aspects comprising a PEG group, the average molecular weights do not include the weight of any terminating group. In aspects comprising a PEG group, the PEG has a formula of $-[CH_2CH_2O]_r-$, where r is an integer selected to provide a PEG group having a mass average molecular weight as described above. In aspects comprising a PEI group, the PEI has a formula of $-[CH_2CH_2NH]_r-$, where r is an integer selected to provide a PEI group having a mass average molecular weight as described above. In aspects where $R^1$ comprises a cyclic $C_{4-5}$heteroaliphatic group, the cyclic $C_{4-5}$heteroaliphatic group can be bound to X of Formula I directly through a bond formed between X and a carbon atom of the cyclic $C_{4-5}$heteroaliphatic group; or it can be bound to X of Formula I through an external carbonyl group (i.e., $-C(=O)-$) of the cyclic $C_{4-5}$heteroaliphatic group. In some such aspects, the cyclic $C_{4-5}$heteroaliphatic group can be a sugar molecule, such as glucuronic acid, trehalose, glucopyranoside, and other sugars, including combinations of such sugars wherein more than one sugar molecule is present (e.g., two to four sugar molecules). In some aspects, $R^1$ comprises 1 to 12 PEG groups, or a combination of 1 to 12 PEG groups and an alkyl group (e.g., $C_{1-5}$ alkyl).

In some aspects, $R^1$ is

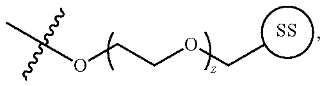

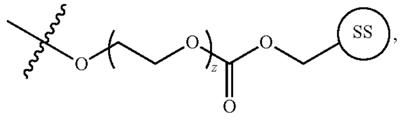

-continued

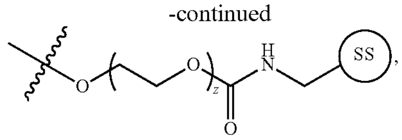, or

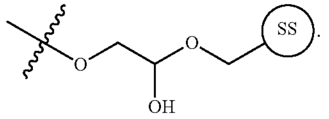.

In any of the aspects in the present disclosure, each of $R^2$ or (one or both of) $R^4$ independently can be an aliphatic group, an aryl group, a polyalkylene oxide, or a polyalkylene amine. In some other aspects, such as when $R^1$ comprises a combination of a heteroaliphatic group and an aliphatic group, one of $R^2$ or (one or both) $R^4$ comprises a PEG group. In particular aspects, $R^2$ is $C_{1-25}$alkyl (e.g., $C_{2-20}$alkyl, or $C_{2-15}$alkyl, or $C_{1-9}$alkyl), phenyl, or naphthyl. In particular aspects, each $R^4$ independently is a $C_{1-10}$alkyl group, such as $C_{1-9}$alkyl (e.g., methyl or ethyl).

In some aspects, $R^3$ is independently is —O—$C_{1-6}$alkyl, —O—$C_{3-6}$cycloalkyl,

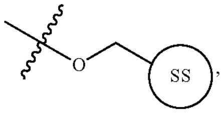, 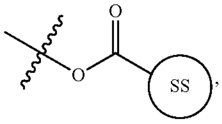,

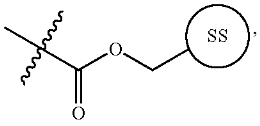, 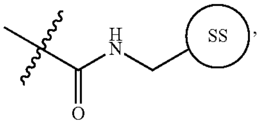,

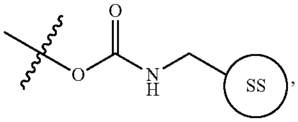,

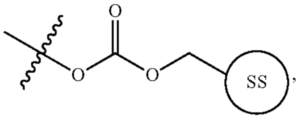,

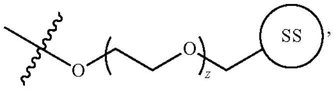,

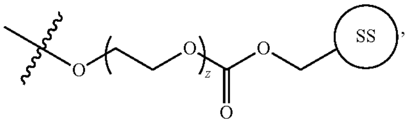,

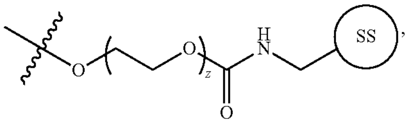, or

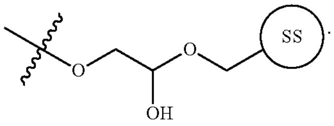.

In some aspects, the solid support (SS) may be selected from agarose resins such as Sepharose, polystyrene resins such as Merrifield resin, Wang resin, and Rink amide resin, polystyrene beads, PEG-based beads such as TentaGel and pegylated-polystyrene beads, silica and silica-gel supports including functionalized silica beads, alumina supports, magnetic silica or polymer-coated magnetic beads, controlled-pore glass beads, functionalized magnetic beads, functionalized silica gel, cellulose and modified cellulose resins, chitosan beads, dextran-based supports such as Sephadex, and pre-functionalized systems including NHS-activated beads, controlled-pore glass beads, maleimide-activated beads, epoxy-activated supports, and streptavidin-biotin capture systems, maleimide-activated beads, and epoxy-activated supports.

In some aspects, the solid support (SS) may be a resin, a bead, a particle, magnetic bead, a non-magnetic bead, an ion exchange matrix, an affinity chromatography matrix, a size exclusion chromatography matrix, a hydrophobic interaction chromatography matrix, an immobilized metal affinity chromatography, a reverse phase chromatography matrix, immunoaffinity chromatography matrix, or a mixed mode chromatography matrix, or any of the solid supports disclosed herein.

In some aspects, $R^1$ is

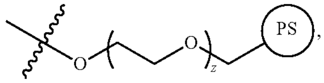,

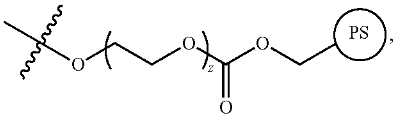,

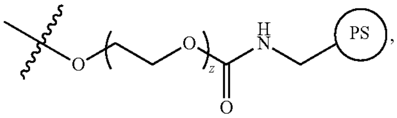, or

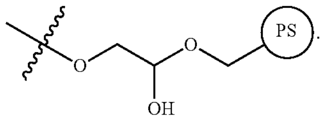.

In some aspects, $R^3$ is independently is —O—$C_{1-6}$alkyl, —O—$C_{3-6}$cycloalkyl,

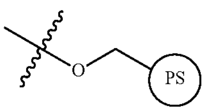, 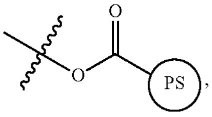,

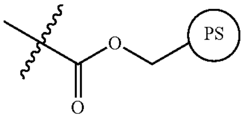, 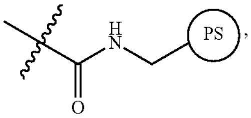,

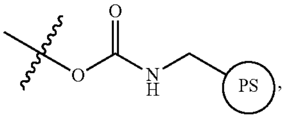, 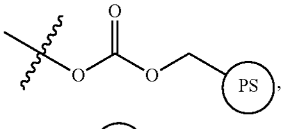,

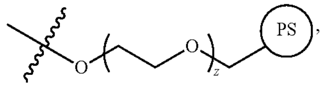,

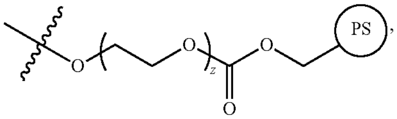,

-continued

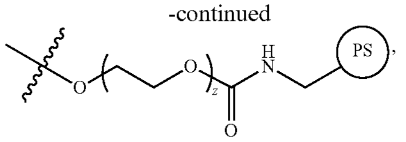

or

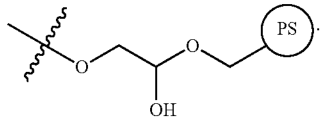

In any of the aspects in the present disclosure, each of $R^2$ or (one or both of) $R^4$ independently can be an aliphatic group, an aryl group, a polyalkylene oxide, or a polyalkylene amine. In some other aspects, such as when $R^1$ comprises a combination of a heteroaliphatic group and an aliphatic group, one of $R^2$ or (one or both) $R^4$ comprises a PEG group. In particular aspects, $R^2$ is $C_{1-25}$alkyl (e.g., $C_{2-20}$alkyl, or $C_{2-15}$alkyl, or $C_{1-9}$alkyl), phenyl, or naphthyl. In particular aspects, each $R^4$ independently is a $C_{1-10}$alkyl group, such as $C_{1-9}$alkyl (e.g., methyl or ethyl).

In any of the aspects in the present disclosure, $R^3$ is selected from an alkoxy group or an aliphatic group (e.g., an alkyl group, an alkenyl group, or an alkynyl group). In some aspects, p is 0, in which case no $R^3$ group is present. In other aspects, p is 1 or 2.

In any of the aspects in the present disclosure, n is 1 and thus the C═Y group is present. In such aspects, Y typically is oxygen or sulfur. In some other aspects, n is 0 and thus the C═Y group is not present and the group bearing X is directly attached to the aryl ring of Formula I.

In some aspects, X is oxygen or NH. In particular aspects, X is oxygen.

In any of the aspects in the present disclosure, the linker is not present and thus X is bound directly to $R^1$. In some other aspects, the linker is present. In such aspects, the linker can be a $C_{1-25}$aliphatic group (e.g., $C_{1-25}$alkyl) or has a structure according to the formula —C(═Z)—W—C(═Z)—X'—, wherein each Z independently can be selected from O, S, or $NR^5$; W can be $C_{1-25}$alkyl, $C_{1-25}$alkenyl, $C_{1-25}$alkynyl, ether, thioether, or amine (e.g., NH, $C_{1-25}$alkyl-N(H)—$C_{1-25}$alkyl); and X' is O, S, or $NR^5$. In particular aspects, the linker, if present, is $—(CH_2)_q—$, $—C(═O)(CH_2)_qC(═O)—O—$, or $—C(═S)(CH_2)_qC(═S)—O—$, $—C(═O)N(H)(CH_2)_qN(H)C(═O)—O—$, wherein each q independently is an integer ranging from 1 to 10.

In any of the aspects in the present disclosure, m is 1, 2, 3, 4, 5, or 6. In particular aspects, m is 1. In any of the foregoing aspects, p is 0, 1, or 2. In particular aspects, p is 0.

In some aspects, the compound can have a structure according to any one of Formulas IA, IB, IC, ID, IE, or IF, illustrated below.

Formula IA

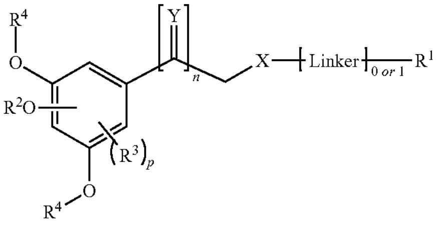

-continued

Formula IB

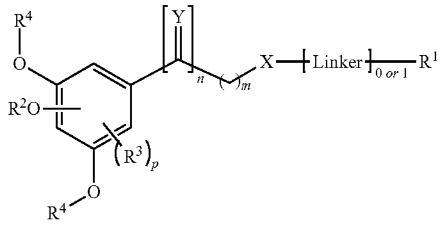

Formula IC

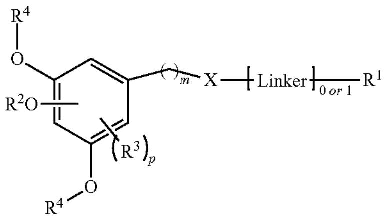

Formula ID

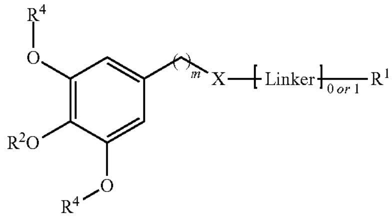

Formula IE

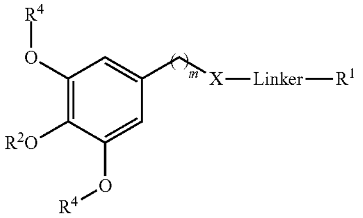

Formula IF

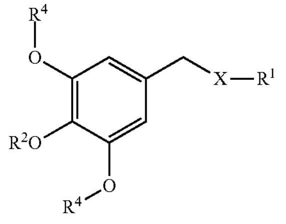

With respect to any of Formulas IA-IF above, each of $R^1$, $R^2$, $R^3$, $R^4$, Y, the linker group, n, m, and p can be as described above for Formula I.

In some aspects, the compound has a structure according to Formulas IG, IH, IJ, and IK, shown below.

Formula IG

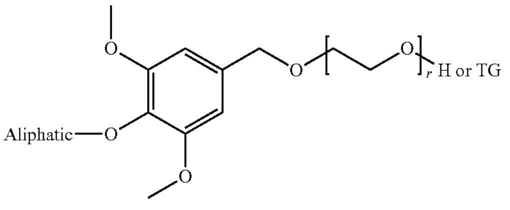

-continued

Formula IH

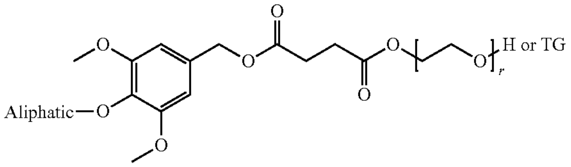

Formula IJ

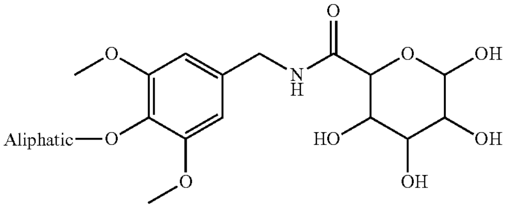

Formula IK

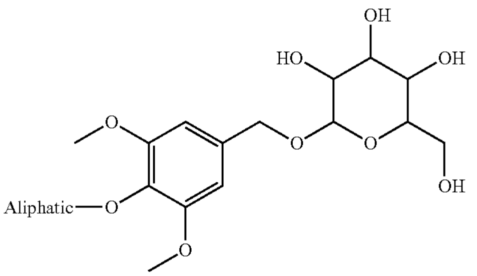

With reference to Formulas IG, IH, IJ, and IK, the aliphatic group is linear, branched, cyclic, or a combination thereof; and the TG group, if present, is an aliphatic group. In particular aspects, the aliphatic group is a linear $C_{2-20}$alkyl group, such as a linear $C_{2-15}$alkyl group, or a linear $C_{2-10}$alkyl group; a branched $C_{2-20}$alkyl group, such as a branched $C_{2-15}$alkyl group, or a branched $C_{2-10}$alkyl group; a cyclic $C_{3-20}$alkyl group, such as a cyclic $C_{3-15}$alkyl group, or a cyclic $C_{3-10}$alkyl group; or a combination of any such linear, branched, and/or cyclic groups. In particular aspects, the aliphatic group is selected from isopentyl, 2-methylpentyl, heptyl, 2,2-dimethylbutyl, pentyl, octyl, nonyl, and the like. The terminating group (or "TG" group) of Formulas IG or IH can be a $C_{1-10}$alkyl group, such as methyl, ethyl, propyl, butyl, pentyl, hexyl, heptyl, octyl, nonyl, or decyl (with any such groups being linear, branched, cyclic, or any combination thereof). In particular aspects, the TG group is methyl. Also with reference to Formulas IG and IH, r is an integer selected to provide a PEG group having a mass average molecular weight as described above for Formula I. In some exemplary aspects, r is an integer selected from 2 to 20, such as 2 to 18, or 2 to 16, or 2 to 14, or 2 to 12, or 2 to 10. In particular aspects, r is 2, 3, 4, 5, 6, 7, 8, 9, 10, 11, 12, 13, 14, 15, 16, 17, 18, 19, or 20.

Representative compound examples are provided in Table 1, below, wherein the "m-PEG" notations are used to indicate the mass average molecular weight of the PEG group (e.g., "m-PEG 550" is used to indicate a number of PEG repeats that provide a mass average molecule weight of 550 g/mol).

11

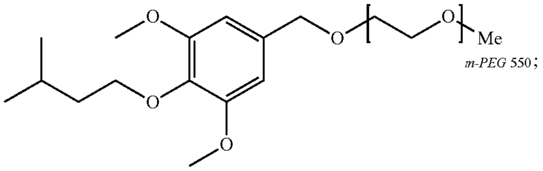

;

12

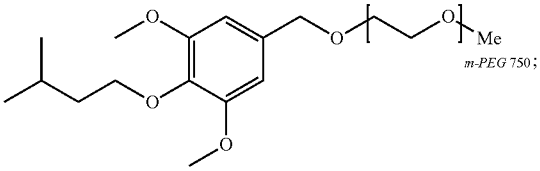

;

13

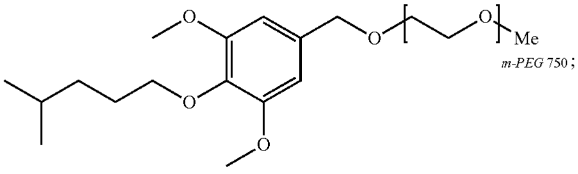

;

14

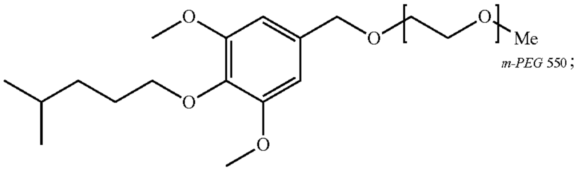

;

15

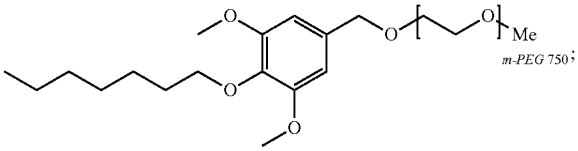

;

16

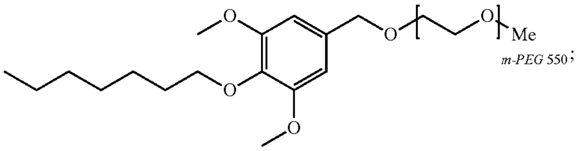

;

17

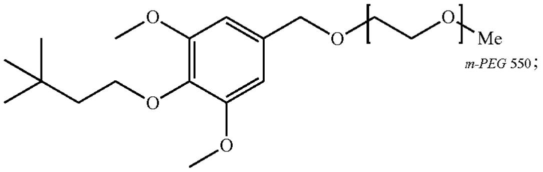

;

18

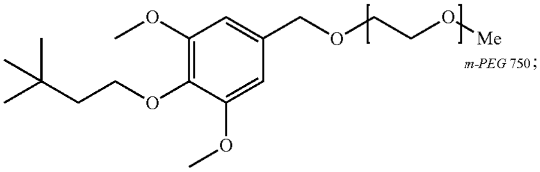

;

-continued
19
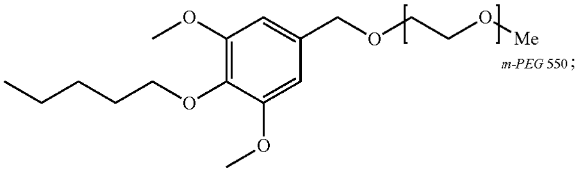
20
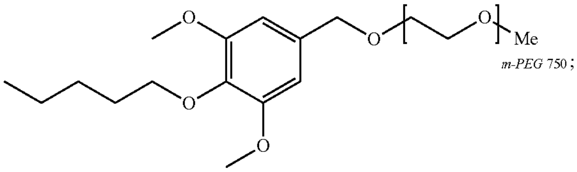
3
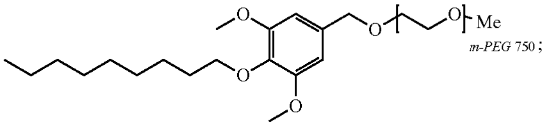
2
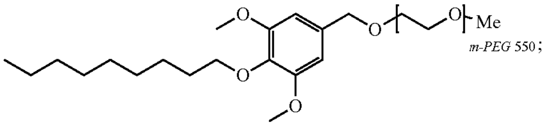
21
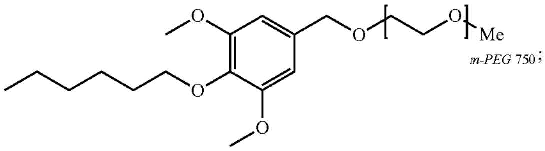
22
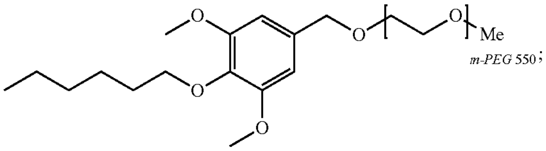
23
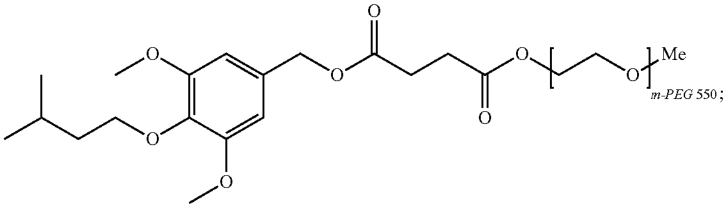
24
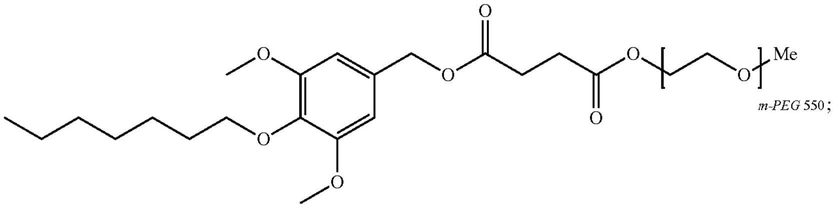
25
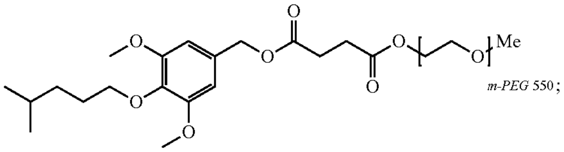
26
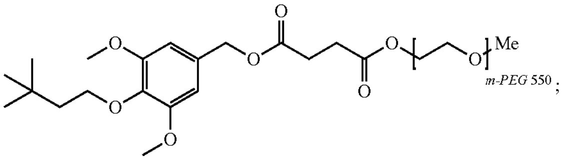
27
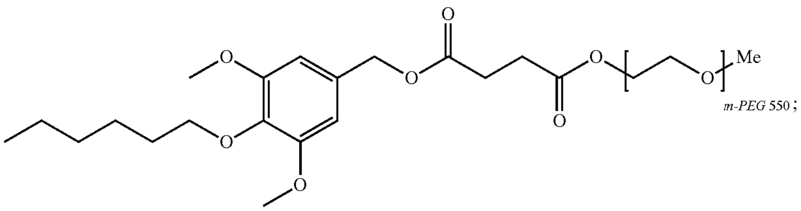
28
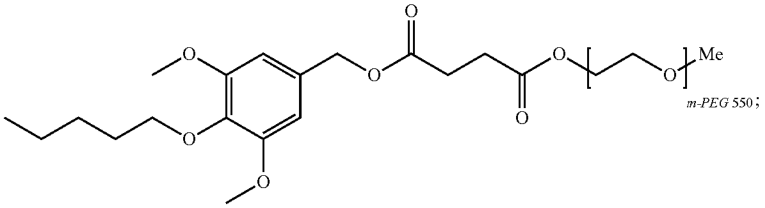

-continued
29
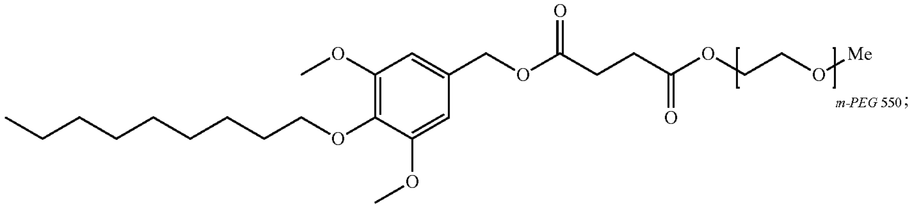
30
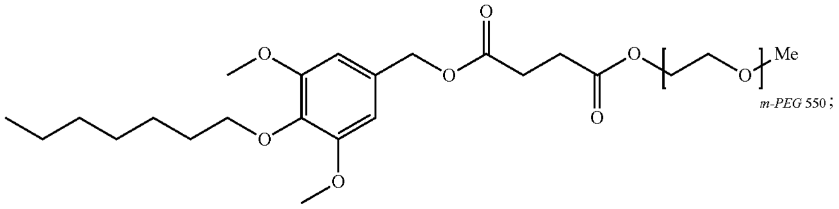
31
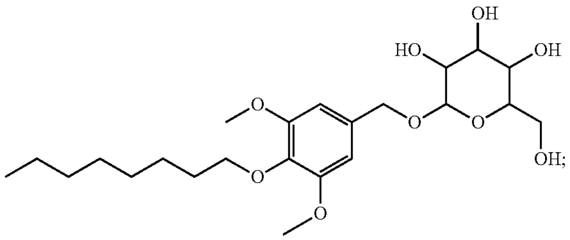
32
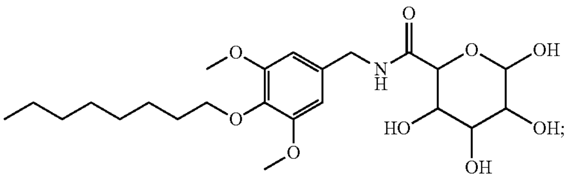
33
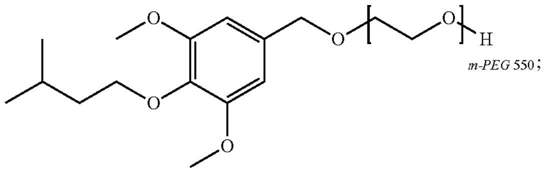
34
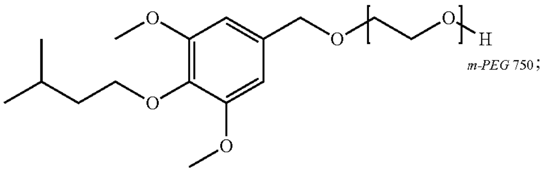
35
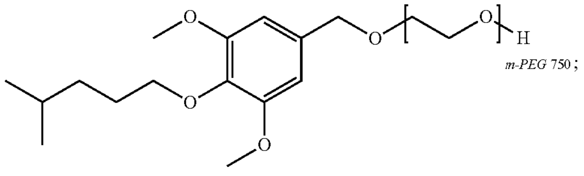
36
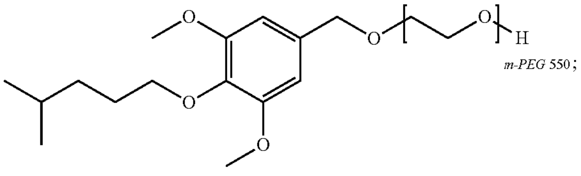
37
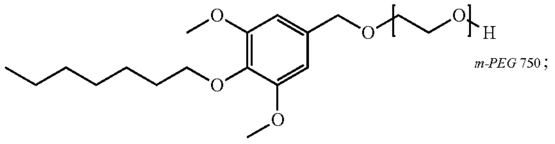
38
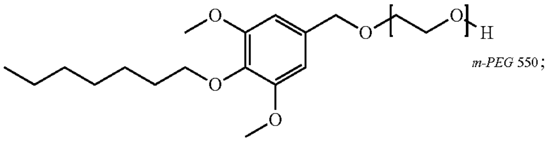
39
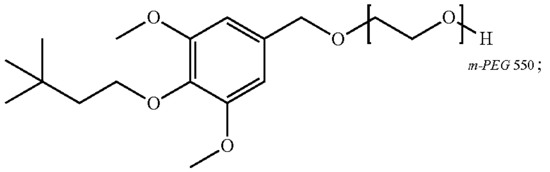
40
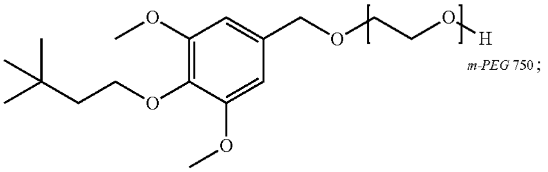
41
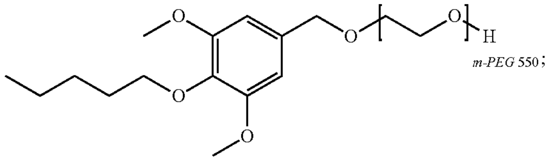
42
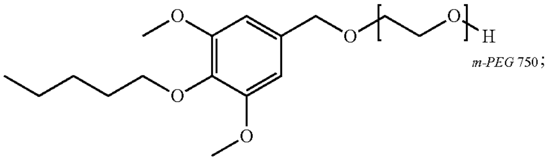

-continued
43
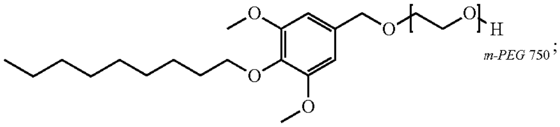
;
44
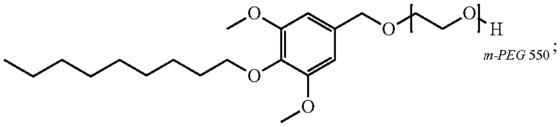
;
45
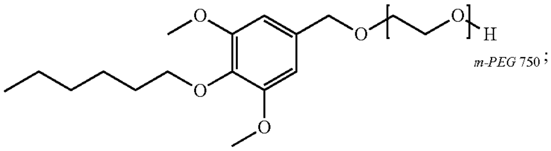
;
46
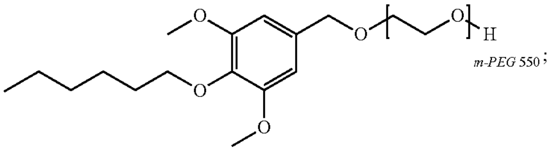
;
47
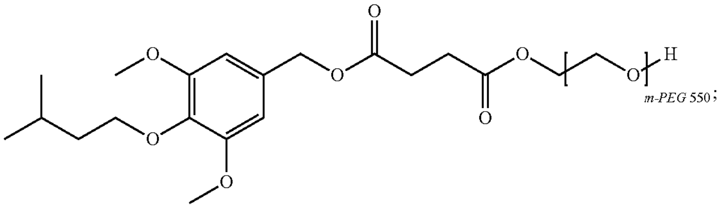
;
48
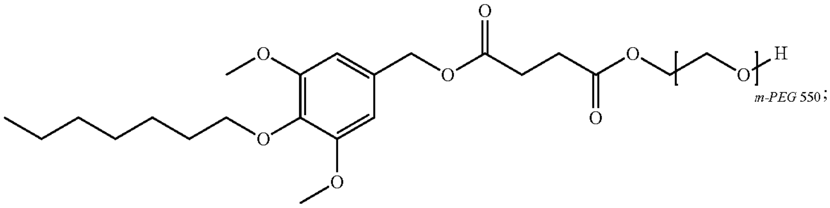
;
49
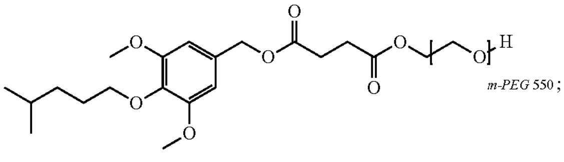
;
50
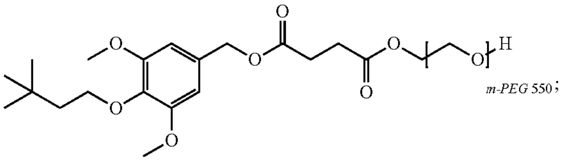
;
51
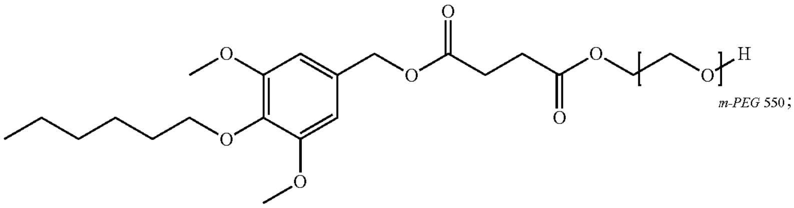
;
52
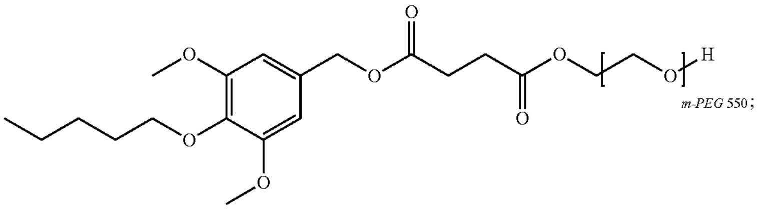
;
53
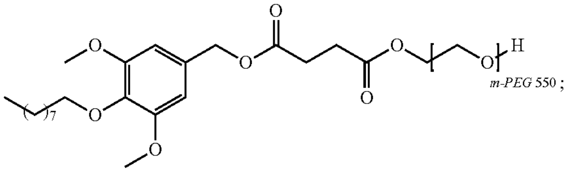
;
54
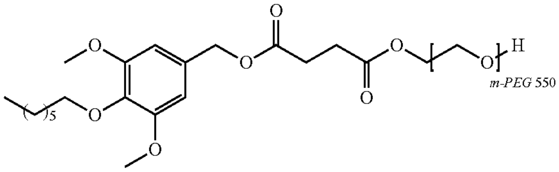
.

Methods

Disclosed herein is a method for making compounds according to the present disclosure. In some aspects, the method comprises performing chemical reactions to add the lipophilic and hydrophilic groups to a core compound, such as that shown in Scheme 1. In some aspects, the method may comprise one or more synthesis steps to add the lipophilic group. In some aspects, the method may comprise one or more, typically two or more, synthesis steps to add the hydrophilic group. In some aspects, the lipophilic group is added by exposing a starting material 100 (Scheme 1) to a base and an $R^2$-group-bearing electrophile, such as an $R^2$-group-bearing halide compound. In some such aspects, the $R^2$-group-bearing halide compound can be a halide-bearing aliphatic compound, such as Br-aliphatic, I-aliphatic, or CI-aliphatic. Starting material 100 is then converted to an $R^2$-bearing intermediate, such as intermediate 102 (Scheme 1). Intermediate 102 can then be converted to a compound according to the disclosure that includes the $R^1$ hydrophilic group using further synthesis steps.

Scheme 1

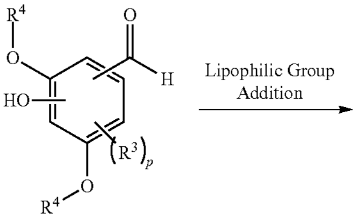

100

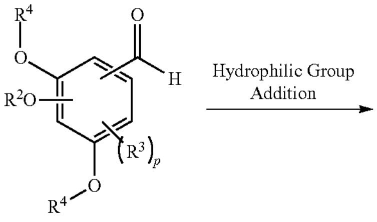

102

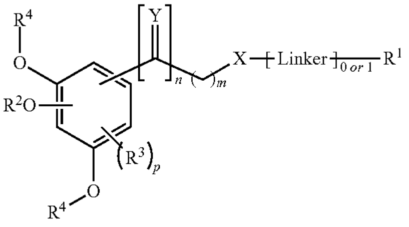

104

In some aspects, intermediate 102 is converted to a compound 104 using a sequence of synthesis steps wherein the aldehyde of 102 is reduced to a hydroxyl group, which is then converted to a suitable leaving group (e.g., a triflate). In such aspects, an $R^1$ group can then be added to displace the leaving group, thus providing a compound according to compound 104, wherein n is 0, m is 1, and wherein the linker is not present. Reagents and conditions used in such aspects are recognizable to those in the art, particularly with the benefit of the present disclosure. For example, in some aspects, a suitable reducing agent (e.g., sodium borohydride) can be used to convert the aldehyde to a hydroxyl group. Then a suitable base (e.g., an amine base) and a suitable leaving group reagent (e.g., methanesulfonyl chloride) can be used to provide the leaving group-containing compound that is reacted with the $R^1$ group.

In yet other aspects intermediate 102 can be converted to a compound 104 by following a similar procedure described above wherein the aldehyde of 102 is reduced to a hydroxyl group. The hydroxyl-containing compound can then be combined with a suitable base and a suitable halide-containing reagent to add the $R^1$ group. For example, in some aspects, the hydroxyl-containing compound can be deprotonated with a suitable base and then allowed to react with an $R^1$-halide reagent, such as a halide-bearing sugar molecule, to provide compound 104, wherein n is 0, m is 1, and the linker is not present. In some such aspects, the halide-bearing sugar molecule can be 2-bromo-6-(hydroxymethyl) tetrahydro-2H-pyran-3,4,5-triol.

In yet other aspects, intermediate 102 can be converted to a compound 104 by following a similar procedure described above wherein the aldehyde of 102 is reduced to a hydroxyl group. The hydroxyl-containing compound can then be combined with a suitable base and a suitable linker (or linker precursor) reagent so as to attach a linker group to the hydroxyl group. In some such aspects, the linker can be an aliphatic halide, an anhydride (e.g., succinic anhydride), or other suitable linker groups. Once added, the linker-containing compound can then be reacted under suitable reaction conditions with a suitable $R^1$-containing group to provide compound 104, wherein n is 0, m is 1, and the linker is present.

In yet other aspects, the aldehyde of compound 100 can be maintained and a suitable $X\text{-[Linker]}_{0\ or\ 1}R^1$ group can be added to the aldehyde using suitable reaction conditions that would be recognized by those in the art with the benefit of the present disclosure. The resulting intermediate could then be oxidized using suitable reagents and reaction conditions to provide a compound 104 wherein N is 1, m is 0 and wherein the linker is or is not present.

With respect to solid-support (SS) bound surfactants, appropriately functionalized hydroxy-substituted syringic acid derivatives, carboxylic acid substituted syringic acid or hydroxymethyl-substituted syringic acid derivatives are converted to PEG-linked constructs bearing terminal amine or hydroxyl groups. These pegylated intermediates are subsequently coupled to functionalized bead surfaces (for example, carboxyl- or epoxy-activated agarose or polystyrene beads or the like) to generate bead-immobilized non-ionic surfactant analogs.

Alternatively, polystyrene beads are modified with poly (ethylene glycol) linkers bearing terminal hydroxyl groups (PS-PEG-OH). Syringic acid derivatives are subsequently coupled to the PEG terminus via ester or carbonate linkages to yield PS-PEG-syringic acid derivatives as solid-support bound surfactants. Polystyrene beads functionalized with carboxylic acid groups

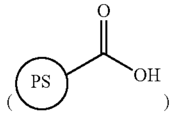

or hydroxy methyl groups

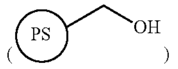

can be used to react with the PEG-alcohols to obtain polystyrene beads with PEG linkers bearing terminal carboxylic acid groups or terminal hydroxy groups.

Applications

The disclosed compounds are useful as surfactants and can be used in many applications where a non-ionic surfactant is suggested or preferred. Applications include, but are not limited to, lysing cells, permeabilizing membranes, inactivating viruses, separating hydrophilic proteins from membranes, reducing surface tension, or decellularizing tissue. Additionally, the disclosed compound may be useful as an excipient or adjuvant in a vaccine, a cleaning agent, a component in buffers particularly biological buffers, a wetting agent, an emulsifier, a surfactant, or as a surface treatment for metals. In some aspects, the disclosed compound can be used for DNA or nucleic acid extraction from blood or pathogens applications, protein expression and purification, ELISA's, Western blotting and RT_PCR applications.

Compounds of this disclosure may be used in a broad range of products and applications across many industries, including but not limited to paint, textiles, metalworking, life sciences, pharmaceutical, industrial, environmental, construction, personal care, and specialty applications. Compounds of the present disclosure may also be useful in the manufacture of a wide range of products, serving as key components in creating surfactant mixtures, coatings, and emulsifier systems that require stable, effective surface activity.

Compounds of this disclosure may be useful as process and finishing aids in the manufacture of industrial raw materials and textiles across chemical, polymer, metallurgical, and biological industries, including as emulsifiers, oil-in-water emulsifiers, water-in-oil emulsifiers, wetting agents, phase transfer agents solubilization agents, viscosity modifiers, thickeners, gelling agents, foaming agents, foam stabilizers, antifoam agents, dispersion agents, micelle-forming agents, foam fractionation agents, cleaning agents, plasticizer systems, anti-static agents, anti-fog agents, anti-block additives, mold-flow modifiers, and resin stabilizers. In other aspects, compounds of this disclosure may be used in the formulations of hydrogels, aerogels, superabsorbent polymers, and polymers. In other aspects, compounds of this disclosure may also be used in biotechnology and enzyme production, such as in fermentation media for biotechnology and enzyme production; in polymer and plastic manufacturing; in metal and mineral processing, for example as collectors, frothers, or modifiers in mineral flotation systems, in degreasing and pickling baths during metal fabrication processes, in slag foaming, flux aids, in pickling and passivation processes, in metal extraction processes, and in metalworking fluid processes; in production of construction materials, such as cements, paints, coatings, and ceramic; in bio-based raw material manufacturing, for example in biorefineries and oleochemical plants; in manufacture, production and finishing of textiles, including leather; in pigment and filler dispersion manufacturing, for example to wet, stabilize, and uniformly distribute solid particles within liquid systems; in paper and pulp manufacturing including for purposes such as deinking, fiber wetting, and cleaning aids; and in water and utility systems used in manufacturing process, including as wetting agents, antifoams, defoamers, and dispersants.

In some aspects, compounds of this disclosure may also be used in the manufacture of polymers and resins; for example, they may be used in emulsion polymerization processes to make a wide range of polymers and resins used in a variety of applications, such as adhesives, paints, paper coating and textile coatings, and monodispersed particles and beads. In other aspects, compounds of this disclosure may be used in controlled radical polymerization processes, including atom transfer radical polymerization, reversible addition-fragmentation chain transfer, and nitroxide-mediated polymerizations, to stabilize dispersed phases, control particle size, solubilize monomers and catalysts, prevent coagulation, and enable high conversion polymerizations in aqueous emulsion, dispersion, and mini-emulsion systems. In other aspects, compounds of this disclosure may be used extensively in electronics and semiconductor manufacturing processes to control wetting behavior, enhance particle removal, stabilize abrasive or nanoparticle dispersions, improve uniformity of photoresist and coating layers, facilitate etching and post-etch cleaning, assist in metal deposition and plating processes, and support defect reduction across wafer fabrication steps. For example, compound of this disclosure may be used in semiconductor cleaning solutions, photoresist stripping formulations, photo developer formulations, etching formulations, chemical mechanical planarization (CMP) slurries, electrode slurries, post-CMP cleaners, wafer cleaners and mask cleaners. In other aspects, compounds of this disclosure can be used in printed circuit board manufacturing baths and cleaners. In other aspects, compounds of this disclosure may be also used in display manufacturing, including coating processes for organic light emitting diodes and light emitting diodes.

In some aspects, compounds of this disclosure may also be used in the manufacturing of batteries, supercapacitors, fuel cells and solar cells. In some aspects, compounds of this disclosure may be used in energy storage and solar technologies to control interfacial behavior, improve material dispersion, and enhance manufacturing consistency across a range of device architectures. In some aspects, for example in batteries, supercapacitors, and fuel cells, compounds of this disclosure may function as electrode slurry and binder dispersants that enable uniform distribution of active materials, conductive additives, and polymers, leading to improved electrode homogeneity and performance. In some aspects, compounds of this disclosure may be incorporated into separator coatings and electrolyte formulations to modify wettability, stabilize interfaces, and reduce defects. In some aspects, for example in solar cell manufacturing—including perovskite and thin-film photovoltaics—compounds of this disclosure may be used to assist in forming smooth, defect-free coatings, improving film morphology, and enabling reliable deposition processes. Through these roles and others, compounds of this disclosure may be used support enhanced efficiency, stability, and manufacturability across modern electrochemical and photovoltaic energy devices.

In other aspects, compounds of this disclosure may be widely used in rubber, elastomer, latex, and tire manufacturing because they provide essential emulsification, wetting, and stabilization functions across multiple process stages. For example, in emulsion polymerized rubbers and acrylic latexes, compounds of this disclosure may be used to help disperse hydrophobic monomers, control particle size, and maintain latex colloidal stability under varying pH, temperature, and shear conditions. In solid rubber and tire compound mixing, compounds of this disclosure may act as processing aids that improve filler dispersion, enhance silica compatibility, reduce mixing energy, and support uniform incorporation of curatives and additives. In latex dipping and rubber article fabrication, compounds of this disclosure may enable consistent wetting, film formation, foam control, and dispersion of pigments and compounding ingredients.

They are also used in post-vulcanization cleaning, mold release systems, and surface treatments to improve adhesion, appearance, and functional performance of finished rubber goods.

In some aspects, compounds of this disclosure may be widely employed in various advanced materials and chemical processing operations due, in part, to their ability to control interfacial phenomena, stabilize dispersed phases, and influence nucleation and growth behavior. In crystal habit modification, in some aspects, compounds of this disclosure may be used to adsorb selectively onto specific crystal faces, thereby altering growth rates and enabling the production of crystals with tailored morphology, size, or purity. In nanoparticle synthesis, compounds of this disclosure may be used to act as steric stabilizers and structure-directing agents, preventing agglomeration of nucleating particles and supporting controlled growth of metal, metal oxide, polymeric, or inorganic nanoparticles. In solvent extraction processes, compounds of this disclosure may facilitate partitioning of hydrophobic solutes by enhancing solubilization and modifying phase boundaries, may be used in cloud point extraction to enable selective concentration or removal of target analytes. In membrane separation systems, compounds of this disclosure may be used as antifouling agents and wetting modifiers, improving membrane performance by reducing deposition of organic or biological materials, enhancing permeability, or stabilizing dispersed feed components. In other aspects, compounds of this disclosure may be used in eluents for chromatographic separations, in supercritical fluid extraction or in other advanced separation processes. In some aspects, for example in spray drying and spray granulation, compounds of this disclosure may be used to reduce surface tension and assist in droplet formation, particle agglomeration, and powder morphology control, improving flowability, solubility, and stability of resulting particulate products. In some aspects, compounds of this disclosure may be used in microencapsulation and controlled-release particle formation to stabilize emulsions or dispersions during capsule formation, promote uniform particle size, and enhance encapsulation efficiency of active ingredients. In some aspects, in heterogeneous catalysis, compounds of this disclosure may be used to stabilize catalyst nanoparticles, control pore structure in catalyst supports, and prevent sintering or deactivation by maintaining uniform dispersion under reaction conditions. Collectively, these functions highlight the versatility of compounds of this disclosure as interfacial engineering agents across diverse chemical, materials, and purification technologies.

In some aspects, for example in environmental and agricultural contexts, there is a particular need for non-ionic surfactants that are readily biodegradable and low-toxicity, for uses in eco-friendly cleaning agents, wastewater formulations, irrigation water treatments, and remediation products and other applications to reduce environmental persistence. In some aspects, compounds of this disclosure may be incorporated into formulations for pesticides, fungicides, herbicides, insecticides and plant growth regulators, including as a means to enhance the wetting and spreading of active ingredients on plant surfaces. They may also be used to facilitate improved adhesion and penetration of active compounds, reduce surface tension, and promote uniform coverage. In some aspects, compounds of this disclosure may be used as a spray mix adjuvant or as an evaporation control agent. In some aspects, compounds of this disclosure may also be used as adjuvants that stabilize emulsions, improve dispersion of micronized solids, and increase biological efficacy while reducing the need for volatile organic solvents. In some aspects, compounds of this disclosure may also be used as soil conditioning agents, as soil penetration enhancers, drift control agents, for example when spraying chemicals, seed treatment agents, and waste-to-energy feedstock conditioning agents. They also may be used in fertilizer coatings, seed coatings, seed treatment agents, and micronutrient delivery systems. In industrial water treatments, non-ionic surfactants may be used as anti-fouling agents, boiler treatment aids, and cooling tower dispersants. They may also be used in algal cultivation to improve dispersion, enhance nutrient and gas transfer, prevent cell aggregation, and maintain stable, uniform growth conditions. One of ordinary skill in this industry can readily appreciate the many uses for compounds of this disclosure, including in groundwater remediations like Surfactant-Enhanced Aquifer Remediation (SEAR), and soil washing; in wastewater and industrial effluent treatment; in bioremediation and microbial enhancement, to aid microbial degradation of hydrophobic pollutants; for environmental cleaning and decontamination applications, including spill response, surface decontamination, and industrial equipment and tank cleaning; and in analytical and environmental monitoring applications, including for example, in micellar electrokinetic chromatography or cloud point extraction, where they may be used for concentrating trace pollutants from water samples. In some aspects, compounds of this disclosure may be used in used in environmental treatment processes to enhance the separation and handling of contaminants in stormwater, runoff, landfill leachate, and sludge management applications. They may function as wetting, dispersing, and conditioning agents that improve solids-liquid separation, support sludge dewatering, and may be paired with foam-control technologies commonly used in wastewater treatment and aeration systems. They may also be used in dust suppression and erosion control applications, including as wetting agents to improve the penetration of water, as binding agents for dusty soils and unpaved roads, or to reduce airborne particulate emissions and soil erosion in places like mining or construction sites. In other environmental applications. In some aspects, compounds of this disclosure may be used in foam fractionation, air stripping enhancements, and in ash wetting agents, like those used, for example, in coal utility processes. In some aspects, compounds of this disclosure may be used in air emission and odor control applications; for example, they may be incorporated into scrubbing solutions in gas treatment systems to capture volatile organic compounds or odorous compounds, by enhancing solubilization of hydrophobic gases or aerosols in the liquid scrubbing medium.

In some aspects, for example, in industrial applications, compounds of this disclosure may be used as pigment wetting agents and stabilizers in coatings and inks, contributing to improved flow, gloss, and film formation. In polymer chemistry, compounds of this disclosure may function as emulsifier mixtures in emulsion polymerization, where they may stabilize latex particles and influence particle size distribution, polymer morphology, and viscosity. In other aspects, compounds of this disclosure may be incorporated into automotive and architectural coatings, industrial lubricants and metalworking fluids, mold release agents, and corrosion inhibitor systems. They may be used to improve pigment dispersion, leveling, and surface smoothness; provide boundary lubrication, corrosion inhibition, and emulsification of oil-water mixtures; reduce surface tension and prevent adhesion between molds and formed materials; and stabilize protective films. In other aspects, compounds of this disclosure may be used in leather, hide or fur processing, including use during processes such as soaking, dehairing, degreasing, tanning, fatliquoring, dyeing and finishing. They may also be incorporated into leather treatment agents, waterproofing, softening or conditioning compositions.

In some aspects, compounds of this disclosure may be used in the construction sector, where a few examples include the integration of non-ionic surfactants into adhesives, sealants, and surface coatings; incorporated into materials such as flooring, tile, bathtubs, drywall, mirrors, insulations, semi-permanent fixtures, roofing materials, and asphalt and bitumen emulsions. Compounds of this disclosure may be incorporated into surface treatments and anticorrosive finishes and act as dispersants, wetting agents and emulsion stabilizers for many applications, and may be used to improve adhesion to various substrates and the uniformity of polymer blends. In some aspects, compounds of this disclosure may be incorporated into concrete, mortar, or grout admixtures as superplasticizers, water reducers, or air-entraining agents.

In some aspects, compounds of this disclosure may be used in bio-decontamination and cleaning applications. In some aspects, they may be used in bio-spill response, for example in biocidal or cleaning formulations. In some aspects, compounds of this disclosure may be used in decontamination of medical, pharmaceutical, veterinary and lab equipment rooms; they may also be used in the decontamination of personal protective equipment and textiles such as gowns, masks, and reusable protective wear. In some aspects, they may be used in the formulation of liquid, paste, and powder cleaning products for industrial, institutional, and household use, including, for example, deodorizers, degreasers, aircraft cleaners, carpet and floor cleaners, dishwashing detergents and liquids, laundry detergents, pet shampoos, pet cleaners, fabric pre-treatment sprays, fabric softeners, fabric conditioners, disinfectant sprays and surface cleaners and wipes, sorbents and spill control kits, eye wash kits, drain and glass cleaners and products, air freshener products, polishes, leather degreasing and surface finishing agents. The low foaming tendency and chemical stability on compounds of this disclosure make them suitable for use for automated cleaning systems and high-performance degreasing applications. They may be used in solvents, chelating agents, and disinfectants, allowing for broad-spectrum cleaning and decontamination applications. Compounds of this disclosure may be used in auto body shampoos, polishes, and detailing products, and in formulations for cleaning and protecting interior surfaces and upholstery.

In some aspects, compounds of this disclosure may be used in specialty and occupational products, such as specialty coatings and surface treatments like aircraft paints, photographic developing chemicals, and medical or dental supplies. In other aspects, compounds of this disclosure may be incorporated into inks, glues, and craft adhesives to improve pigment dispersion, flow, and uniform drying. In 3D or additive manufacturing, it can be used in printing resins, printing inks, printing binders, printing powders, photopolymer resins, binder-jet inks, powder-bed wetting, post-processing cleaners. In writing instruments, compounds of this disclosure may be used to aid in the maintenance of ink fluidity and prevent clogging of delivery mechanisms.

In other aspects, compounds of this disclosure may be used in household maintenance products such as concrete patching compounds, primers, paint and finish removers, degreasers, paints, primers, surface sealants, septic system treatment products, antiscalants, and generally in products where there is a need to emulsify organic residues and promote biodegradation. In other aspects, compounds of this disclosure may be used in personal care products and cosmetics, including in products such as hair coloring, ostomy products, after-sun care products, wound care products, micellar water, shampoos, hair styling products, soaps, body washes and gels, bath and body oils, facial cleansers and moisturizers, perfumes, deodorants, anti-perspirants, sunburn treatment products, facial masks, body and face scrubs, toners, nail and cuticle care products, products for treating muscle or joint pain, makeup products, sterilization products, contact lens cleaners, lens wetting solutions, and lotions. In other aspects, compounds of this disclosure may be used in oral care products, such as in toothpaste, tooth powder, mouthwash, oral rinse, dental gel, denture cleaner, denture adhesives, interdental cleaners, and oral care foams; they may also be used in the coating for dental floss.

In other aspects, compounds of this disclosure may be used in autobody work products, such as cleaners, polishers, washes and shampoos. In other aspects, compounds of this disclosure may be used to act as a dispersant, friction modifier, antiwear additive, or emulsifier in many lubricants, such as engine oil, crankcase oil, gear oil, transmission fluid, hydraulic fluid, compressor oil, or grease.

In some aspects, compounds of this disclosure may be used in the food and beverage manufacturing and production industry for a number of applications, including improving texture, shelf life, and uniformity of food products. For example, they may be used as foaming agents, antifoaming agents, defoaming agents, food emulsification agents, and stabilizing agents. They may be used to create and stabilize emulsions between immiscible ingredients like oil and water; as solubilizers to enable homogenous blending; as dispersal agents, for example to disperse flavors, colors and vitamins in aqueous media; as antifoaming agents during food processes such as fermentation, bottling, or frying; as wetting and coating agents to facilitate even distribution, for example in food glazing, pan coatings, and dough conditioners; and in cleaning and sanitation products. Compounds of this disclosure may also be used in food packaging adhesives or food packaging coatings. In other aspects, compounds of this disclosure may be used in animal feed, pet food, aquaculture feed, or nutritional supplements; for example, they may be used as emulsifiers, stabilizers, or wetting agents in feed premixes, liquid feeds, or medicated feeds.

In some aspects, compounds of this disclosure may be used in pharmaceutical and biotechnological industries, where they may be used as solubilizers, emulsifiers, wetting agents, and stabilizers in pharmaceutical and biotechnological formulations. In some aspects, they may also be used as stabilizers and protectors, including to prevent crystallization, aggregation, or denaturation of proteins, vaccines, and biologics during formulation and storage. In some aspects, they may be used in pharmaceutical manufacturing, including as antifoaming and processing agents, or in pharmaceutical-grade cleaning formulations. Their mild nature allows for protein solubilization, membrane permeabilization, and stabilization of labile compounds. In some aspects, compounds of this disclosure may also be used as cryopreservation agents to stabilize cell membranes, reduce ice crystal-induced damage, and improve the uniform distribution and penetration of cryoprotective compounds during freezing and thawing. In some aspects, compounds of this disclosure may be used during manufacturing for various clean-in-place and sterilize-in-place operations; they may also be used in buffers during chromatographic purification, filtration, microfiltration or ultrafiltration steps. In some aspects, in veterinary and human pharmaceuticals, they may be used to improve bioavailability and stability of hydrophobic actives. They may be included in drug delivery systems, biologics, and excipient formulations. They may also be used to prevent crystallization, aggregation, or denaturation of proteins, vaccines, and biologics during formulation and storage. In some aspects compounds of this invention may be used in various formulations, including parenteral formulations, such as injectables or intravenous emulsions, liposomes, or nanoemulsions; inhalation and nasal formulations; ophthalmic formulations, topical gels, creams or ointments; and in transdermal patches and suppositories.

In some aspects, compounds of this disclosure may be used in various aspects of medical device design, manufacture, and performance enhancement due, in part, to their ability to modify surface properties without imparting charge or ionic residues. Compounds of this disclosure may be used for cleaning and surface preparation of device substrates to remove contaminants and improve coating adhesion; as wettability enhancers and dispersing agents in hydrophilic or drug-eluting coatings; and as stabilizers in emulsions or polymer-drug formulations. Compounds of this disclosure may be used to improve biocompatibility by reducing protein adsorption and biofouling on device surfaces, while maintaining chemical stability through sterilization processes. They may be incorporated into coating compositions, processing baths, or formulation media to achieve controlled surface energy, uniform coating morphology, and consistent therapeutic performance across a range of medical devices such as catheters, stents, and implantable components. They may be used as surface-modifying primers and adhesion promoters for medical device assemblies. They may also be incorporated as components or adjuvants of biocides, antimicrobial coatings, surface disinfectants, or instrument cleaners.

In some aspects, compounds of this disclosure may be used in numerous applications in fuels, fuel production processes, and fuel additive technologies due to their ability to modify interfacial properties, enhance dispersion, and improve overall fuel system performance. For example, in gasoline, diesel, jet, marine, and biofuel formulations, compounds of this disclosure may be used as dispersants that help prevent or remove deposits on injectors, intake valves, and combustion surfaces, thereby maintaining engine cleanliness and efficiency. In other aspects, compounds of this disclosure may be incorporated into deposit-control additives and injector-cleaner packages to stabilize contaminants, solubilize gums, and reduce particulate agglomeration. In other aspects, compounds of this disclosure may be used in in distillate fuels, for example to serve as cold-flow improvers that influence wax crystal morphology to enhance low-temperature operability, as well as demulsifiers that promote separation of water from fuel to protect storage and engine systems. Additionally, compounds of this disclosure may act as lubricity improvers, forming boundary films that reduce wear in low-sulfur and ultra-low-sulfur fuels. In other aspects, compounds of this disclosure may be used in fuel production processes, for example in desalting or treating processes. These diverse functionalities make compounds of this disclosure key components for optimizing stability, handling, and performance across modern fuel and fuel-additive applications.

In other aspects, compounds of this disclosure may be used widely in the energy, oil and gas, and mining industries, where they may be incorporated into numerous formulations including drilling muds and fluids, completion fluids, enhanced oil recovery (EOR) agents, demulsifiers, and cleaning compositions. In some aspects they may be used as dispersants and wax/paraffin inhibitors; as corrosion inhibitors and scale inhibitors for production and refining streams; as bitumen and heavy oil emulsifiers; or as oil sands processing aids. In some aspects, in enhanced oil recovery applications, compounds of this disclosure may be used to reduce interfacial tension between crude oil and injected aqueous phase, including to facilitate mobilization of residual oil otherwise trapped after primary and secondary recovery stages, to improve sweep efficiency during water flooding or chemical flooding operations, and increase total hydrocarbon recovery. During crude oil production, compounds of this disclosure may be used in a number of ways, including as demulsifiers to destabilize and resolve unwanted emulsions which can form for a variety of reasons, including due to natural surface-active constituents such as asphaltenes, resins, and organic acids. They may be used to promote coalescence of dispersed water droplets and facilitate phase separation in separators and treaters. Compounds of this disclosure may also be incorporated into stimulation and cleaning treatments, including acidizing and hydraulic fracturing fluids. In these systems, compounds of this disclosure may reduce surface tension and alter rock wettability, enhancing fluid penetration into formation pores and removal of organic deposits such as paraffins or asphaltenes. In other aspects, in pipeline and equipment cleaning, compounds of this disclosure may be used as dispersants and detergents that emulsify hydrocarbon residues and sludge, thereby maintaining flow efficiency and mitigating corrosion.

In each of the foregoing applications, a person of ordinary skill in the art will readily understand how to choose from the compounds disclosed to select a compound with an HLB such that the surfactant is suitable for the use they intend. Moreover, one skilled in the art will readily understand how to use routine testing for the selected compound of this disclosure to establish the parameters required for using the compounds of this disclosure in the various disclosed uses.

Nonionic surfactants, for example Triton™ X-100, Nonidet™ NP-40, and Tergitol™ NP-40, are employed widely across many industries. However Triton™ X-100, Nonidet™ NP-40, and Tergitol™ NP-40 present environmental and toxicological concerns, including potential endocrine-disrupting properties, aquatic toxicity, and bioaccumulation associated with their structures. Regulatory restrictions—particularly within the European Union under REACH and environmental directives—have prompted the search for safer, high-performance alternatives. Compounds of the present disclosure are such alternatives OECD 236 Fish Embryo Acute Toxicity (FET) test provides a standardized method for assessing the acute aquatic toxicity of chemical substances using early-life stages of fish. In this test, fertilized eggs—typically from *Danio rerio* (zebrafish)—are exposed to defined concentrations of a substance, and developmental endpoints such as coagulation, absence of somite formation, lack of heartbeat, and non-hatching are monitored over a 96-hour period. The resulting effect concentrations, including the $LC_{50}$—the concentration of a substance causing lethal effects in 50% of embryos—offer quantitative measures of toxic potency that support regulatory hazard classification and environmental risk assessment. In some aspects, compounds of this disclosure may have a higher $LC_{50}$ than Triton™ X-100, Nonidet™ NP-40, and Tergitol™ NP-40. In some aspects, compounds of this disclosure may have a $LC_{50}$ at a concentration equal to or greater than 0.05, 0.1, 0.3, 0.5, 1, 2, 3, 5, 10, 15 or 20 mg/L.

*Daphnia* aquatic toxicity tests provide a standardized and sensitive method for evaluating the potential harmful effects of chemical substances on freshwater invertebrates, serving as an early indicator of ecological risk. In these assays, *Daphnia magna* or *Daphnia pulex* are exposed to defined concentrations of a test material under controlled conditions, and their immobilization or mortality is measured over a fixed period, typically 24 to 48 hours. The resulting effect concentrations, such as the $EC_{50}$—the concentration causing immobilization in 50% of the test organisms within 48 hours—enable quantitative comparison of toxic potency across substances and support regulatory classification of environmental hazards. By offering high reproducibility, well-characterized biological sensitivity, and rapid results, *Daphnia* tests play a crucial role in screening and differentiating product candidates, informing safe-by-design efforts, and ensuring compliance with international aquatic toxicity requirements. Triton™ X-100, Nonidet™ NP-40, and Tergitol™ NP-40 have a low $EC_{50}$. By-products of Formula I result in significantly higher $EC_{50}$ as compared to Triton™ X-100, Nonidet™ NP-40, and Tergitol™ NP-40. In some aspects, compounds of this disclosure have higher $EC_{50}$—that is, they will not reach 50% immobilization until higher concentrations—as compared to Triton™ X-100, Nonidet™ NP-40, and Tergitol™ NP-40. In some aspects, compounds of this disclosure have an $EC_{50}$ equal to or greater than 0.5, 1, 2, 3, 4, 5, 7.5, 10, 12, 15, or 20 mg/L, when tested under a *Daphnia* test.

The OECD 301B $CO_2$ Evolution Test provides a standardized and highly reliable method for determining the ready biodegradability of organic substances by quantifying the carbon dioxide evolved during microbial degradation under controlled aerobic conditions. By comparing the measured $CO_2$ production to the theoretical maximum expected from complete mineralization, the test delivers a clear, quantitative indication of a substance's environmental persistence. This method offers significant regulatory and practical benefits, including reproducible assessment across different chemical classes, early identification of environmentally benign product candidates, and support for compliance with global environmental safety requirements. The test's sensitivity and well-defined criteria enable developers to evaluate biodegradation performance with confidence, facilitating the design and selection of materials that minimize long-term ecological impact. A substance is determined to be "readily biodegradable" under OECD 301b if it has achieved a 60% biodegradability result, which is equivalent to 60% of ThOD (theoretical oxygen demand) or ThCO2 (theoretical carbon dioxide) production within a ten-day window during a 28-day test. Triton™ X-100, Nonidet™ NP-40, and Tergitol™ NP-40 have failed to achieve a 60% biodegradability result, leading to a desire to find effective non-ionic surfactants with a more favorable biodegradability profile. In some aspects, compounds of this disclosure may achieve a biodegradability result that is higher than Triton™ X-100, Nonidet™ NP-40, or Tergitol™ NP-40. In some aspects, compounds of this disclosure may achieve a 60% biodegradability result, as measured according to OECD 301b. In other aspects, compounds of this disclosure may have a biodegradability result that is equal to or greater than 20%, 25%, 30%, 40%, 50%, 60%, 65%, 70%, 75%, 80%, 85%, 90%, 95%, or 100% biodegradability result, as measured according to OECD 301b.

In one aspect, the disclosed compounds are useful in methods comprising cell lysis. In some aspects, the method comprises treating the cell with the disclosed compound(s) to facilitate cell lysis.

In one aspect, the disclosed compounds are useful in methods for virus inactivation, particularly inactivating a virus having a lipid envelope, or a virus that may develop a lipid envelope. In some aspects, a method for inactivating a virus comprises combining the disclosed compound with a liquid comprising the virus.

Also disclosed herein are aspects of a kit comprising a compound disclosed herein.

Overview of Several Aspects

Disclosed herein is a compound having a structure according to Formula I,

Formula I

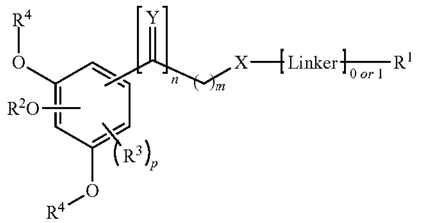

wherein:

$R^1$ is a hydrophilic group;

$R^2$ is a lipophilic group;

X is selected from oxygen, sulfur, or $N(R^5)$;

$R^3$ is selected from heteroaliphatic, aliphatic, or aryl;

each $R^4$ independently is aliphatic;

Y is selected from oxygen, sulfur, or $N(R^5)$;

the linker, when present, is aliphatic or has a formula —C(=Z)—W—C(=Z)—X', wherein each Z independently is oxygen, sulfur, or $NR^5$, W is an aliphatic or heteroaliphatic group, and X'O is oxygen, sulfur, or $NR^5$;

n is an integer selected from 0 or 1;

m is an integer selected from 0 to 6, provided that, if n is 0, then m is 1;

p is an integer selected from 0 to 2; and each $R^5$ group independently is selected from hydrogen, aliphatic, aromatic, or heteroaliphatic.

In any or all of the above aspects, the compound may have a structure according to any one of Formulas IA-IF Formula IA

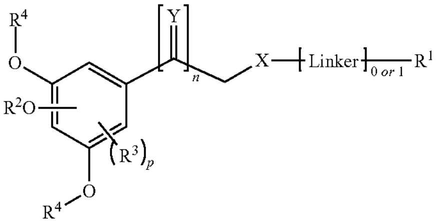

Formula IB

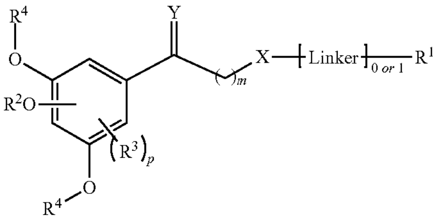

-continued

Formula IC

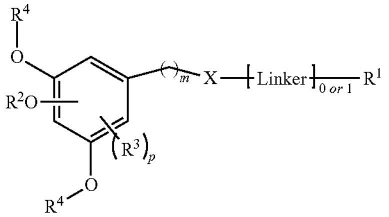

Formula ID

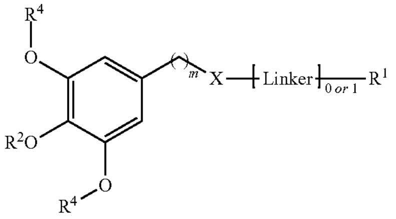

Formula IE

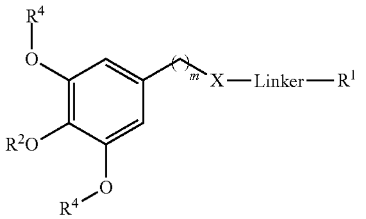

Formula IF

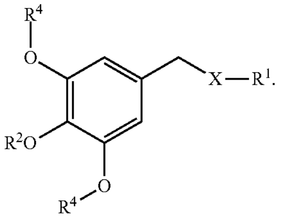

In any or all of the above aspects, the $R^1$ and $R^2$ groups may be selected to provide a hydrophilic-lipophilic balance value ranging from 10 to 18.

In any or all of the above aspects, the $R^1$ group comprises a heteroaliphatic group.

In any or all of the above aspects, the heteroaliphatic is a linear heteroaliphatic group.

In any or all of the above aspects, the linear heteroaliphatic group is a polyalkylene oxide.

In any or all of the above aspects, the linear heteroaliphatic group is a PEG group having a mass average molecular weight ranging from 500 g/mol to 800 g/mol.

In any or all of the above aspects, $R^1$ may comprise a cyclic heteroaliphatic group.

In any or all of the above aspects, the cyclic heteroaliphatic group may comprise a sugar molecule.

In any or all of the above aspects, $R^2$ may comprise an aliphatic group or an aryl group.

In any or all of the above aspects, $R^2$ may comprise $C_{2-25}$alkyl, phenyl, or naphthyl.

In any or all of the above aspects, the $C_{2-25}$alkyl group is linear, branched, cyclic, or a combination thereof.

In any or all of the above aspects, p may be 1 or 2 and each $R^3$ independently may comprise an alkoxy group or an aliphatic group.

In any or all of the above aspects, each $R^4$ independently may comprise a $C_{1-10}$alkyl group.

In any or all of the above aspects, each $R^4$ independently may comprise a methyl or ethyl.

In any or all of the above aspects, n may be 1 and Y is oxygen or sulfur.

In any or all of the above aspects, X may be oxygen or NH.

In any or all of the above aspects, X may be oxygen.

In any or all of the above aspects, the linker may not be present.

In any or all of the above aspects, the linker may be present and is a $C_{1-25}$aliphatic group.

In any or all of the above aspects, the linker may be present and has a structure according to the formula $—C(=Z)—W—C(=Z)—X'—$, wherein each Z independently is selected from O, S, or $NR^5$; W is $C_{1-25}$alkyl, $C_{1-25}$alkenyl, $C_{1-25}$alkynyl, ether, thioether, or amine; and X' is O, S, or $NR^5$.

In any or all of the above aspects, the linker may be present and is $—(CH_2)_q—$, $—C(=O)(CH_2)_qC(=O)—O—$, or $—C(=S)(CH_2)_qC(=S)—O—$, $—C(=O)N(H)(CH_2)_qN(H)C(=O)—O—$, wherein each q independently is an integer ranging from 1 to 10.

In any or all of the above aspects, m may be 1 and p may be 0.

In any or all of the above aspects, the compound may have a structure according to any one of Formulas IG, IH, IJ, or IK Formula IG

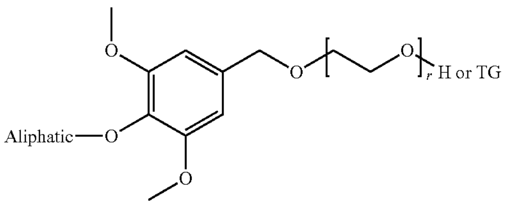

Formula IH

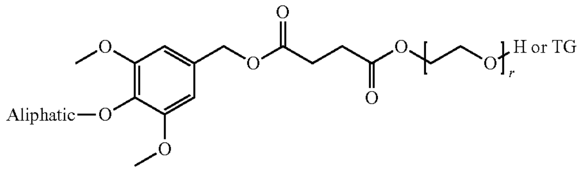

Formula IJ

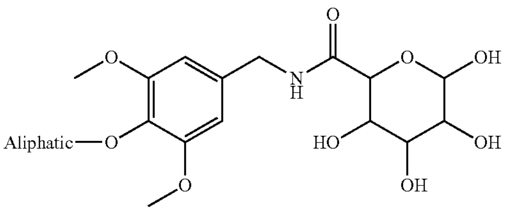

Formula IK

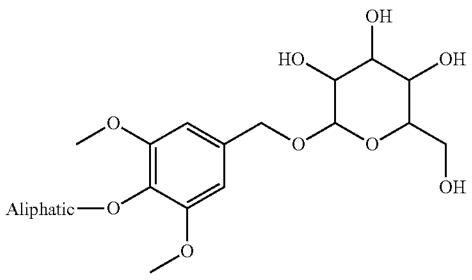

wherein the aliphatic group is linear, branched, or cyclic, or a combination thereof; TG, if present, is a terminating group that is an aliphatic group; and r is an integer selected from 2 to 20.

In any or all of the above aspects, the aliphatic group may comprise a linear $C_2$-20alkyl group; a branched $C_{2-20}$alkyl group; a cyclic $C_{3-20}$alkyl group; or a combination of any such linear, branched, and/or cyclic groups.

In any or all of the above aspects, the aliphatic group may comprise isopentyl, 2-methylpentyl, heptyl, 2,2-dimethylbutyl, pentyl, octyl, or nonyl.

In any or all of the above aspects, the TG group may comprise a $C_{1-10}$alkyl group.

In any or all of the above aspects, the TG group may comprise a methyl.

In any or all of the above aspects, the compound may be selected from any one of the compounds 1 to 54 disclosed herein.

Also disclosed is a method, comprising exposing a sample to a compound disclosed herein and/or according to any or all of the above aspects.

In any or all of the above aspects, the sample may comprise a biological sample.

In any or all of the above aspects, the sample may comprise a cell. The cell may be solubilized and/or permeabilized.

Also disclosed is a method of lysing a cell, comprising contacting the cell with an amount of a compound disclosed herein and/or according to any or all of the above aspects sufficient to facilitate cell lysis.

Also disclosed is a composition, comprising a compound disclosed herein.

Also disclosed is a kit, comprising a compound disclosed herein and a container.

EXAMPLES

A representative procedure for making compounds according to the present disclosure is described below in Examples 1-4. One or more procedures according to Examples 1-4 can be used to prepare other compounds disclosed herein by exposing a suitable starting material to different aliphatic halides and then performing similar conversion steps from the aliphatic-substituted intermediate to the final product (that is, similar conversion steps as outlined in Examples 2-4). Other examples can utilize other synthetic methods described herein.

Example 1

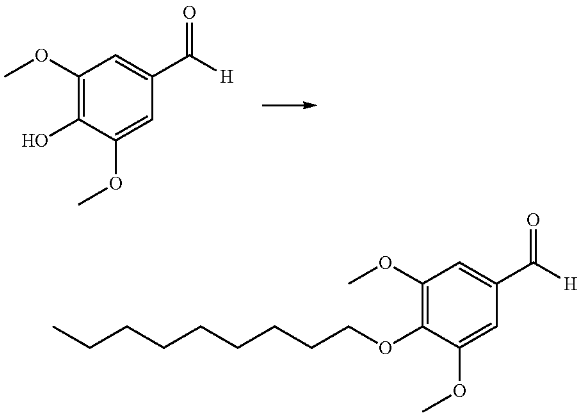

Syringaldehyde (100.16 g, 550 mmol) was dissolved in anhydrous dimethylformamide (400 mL) in a three neck 2000 mL RB flask. The mixture was stirred via mechanical stirrer at a rate of 100 RPM. Potassium carbonate (151.7 g, 1100 mmol) was added in one portion, and the reaction was heated to 110 °C for 30 minutes. The temperature was then set to 80 °C during which 1-Bromononane (209.8 mL, 1100 mmol) was added dropwise via dropper funnel over the course of 1 hr while the reaction was cooling to 80 °C Once the addition was complete, the reaction was stirred at 80 ° C. for 3 hr at which point full consumption of the starting material was observed via TLC (50% EtOAc:Heptane). The reaction was then cooled to room temperature before excess potassium carbonate was filtered off. The filtrate was collected and concentrated to dryness. The residue was then dissolved in EtOAc (400 mL), and the organic layer was washed with 1 M HCl (1×400 mL), followed by a wash with brine (1×400 mL). The organic layer was then dried with anhydrous magnesium sulfate before being concentrated to dryness to yield the crude product as a brown oil. The crude material was placed at −20° C. for 12 hr at which point the material solidified. Heptane (200 mL) was added to the crude product and stirred vigorously for 30 min at RT. The material was then filtered and the solid was washed with Heptane (1x100 mL). The solid product was collected as a white crystallize solid (92.2 g, 54.4%).

Example 2

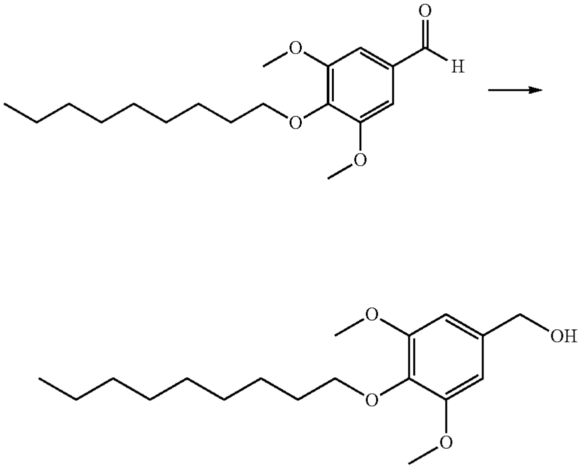

3,5-dimethoxy-4-(nonyloxy)benzaldehyde (139.85 g, 453 mmol) was dissolved in 200 proof ethanol (750 mL) in a three neck 2000 mL RB flask and stirred at 300 RPM. The mixture was cooled to 4 °C in an ice bath. Sodium borohydride (39.77 g, 906 mmol) was added portion wise over the course of 5 min. The reaction was then stirred at 4° C. for 1.5 hr until full consumption of the starting material was observed via TLC (50% EtOAc:Hep). Once complete, the reaction was concentrated to dryness, and the residue was dissolved in EtOAc (400 mL). The organic layer was washed successively with water (1×400 mL), and brine (1×400 mL), before being dried with anhydrous magnesium sulfate. The organic layer was then concentrated to dryness to yield the desired product as a yellow oil (133.48 g, 94.7%).

Example 3

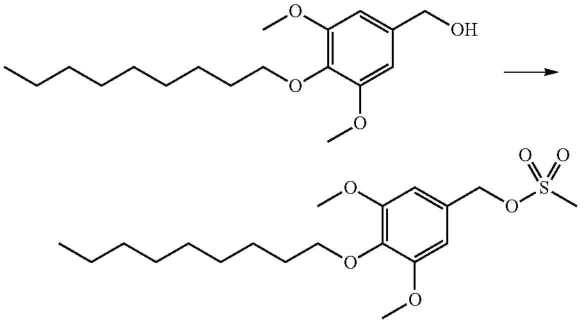

(3,5-dimethoxy-4-(nonyloxy)phenyl) methanol (34.01 g, 121 mmol) was dissolved in anhydrous dichloromethane (400 mL) in an oven dried single neck 1 L RB flask and stirred at 200 RPM. The mixture was cooled to 4 °C in an ice bath. Triethylamine (30.3 mL, 242 mmol) was added dropwise via dropper funnel over the course of 10 minutes. The reaction was then stirred for 5 minutes before a mixture of methanesulfonyl chloride (12.7 mL, 181.5 mmol) in anhydrous dichloromethane (30 mL) was added dropwise via dropper funnel over the course of 15 minutes. The reaction was then allowed to warm to room temperature and stirred for 18 hr at which point full consumption of the starting material was observed via TLC (50% EtOAc:Hep). The reaction was then transferred to a separatory funnel and washed with brine (1×400 mL). The organic layer was dried with anhydrous magnesium sulfate before being concentrated to dryness to yield the crude product as a brown semisolid. The crude product was carried forward to the next reaction without purification. (44.95 g, 95.4%).

Example 4

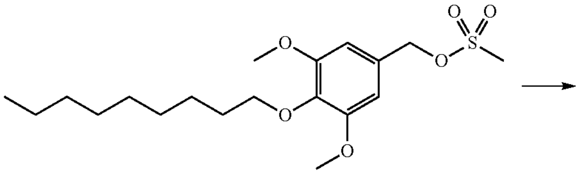

-continued

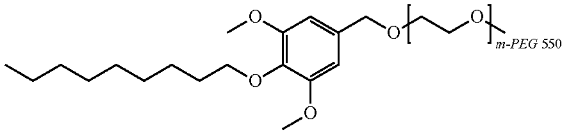

Compound 2 (SY-210)

Poly(ethylene glycol) methyl ether mass average molecular weight 550 (24.4 g, 44.4 mmol) was dissolved in anhydrous tetrahydrofuran (112 mL) in an oven dried 500 mL single neck RB flask and stirred at a rate of 250 RPM. Potassium tert-butoxide (7.5 g, 44.4 mmol) was added portion wise over the course of 1 minute. The mixture was then cooled to 4° C. in an ice bath. 3,5-dimethoxy-4-(nonyloxy)benzyl methanesulfonate (11.5 g, 29.6 mmol) was dissolved in anhydrous tetrahydrofuran (42 mL) and added dropwise to the reaction via dropper funnel over the course of 10 minutes. The reaction was then warmed to room temperature for 18 hr at which point full consumption of the starting material was observed via TLC (50% EtOAc:Hep). The reaction was then concentrated to dryness and the residue was dissolved in EtOAc (200 mL). The organic layer was then washed successively with water (1×200 mL) and brine (1×200 mL). The organic layer was dried with anhydrous magnesium sulfate before being concentrated to dryness. The crude product was then dissolved in a minimal amount of methanol before being loaded onto a Biotage Sfar silica column without the use of a precolumn before being separated by Biotage: MeOH:DCM 0-0% (2 CV), 0-15% (18 CV). The fractions containing the desired product, compound 2 were collected to yield pure product as a yellow oil (16.9 g, 79.0%). The structure of compound 2 was confirmed by $^1$H NMR (400 MHz, $CDCl_3$) δ 6.395 (s, 2H), 4.327 (s, 2H), 3.783-3.741 (t, J=6.88 Hz, 2H), 3.671 (s, 6H), 3.501-3.469 (m, 22H), 3.211 (s, 3H), 1.608-1.534 (m, 2H), 1.299-1.235 (m, 2H), 1.170-1.096 (m, 12H), 0.727-0.688 (m, 3H).

Example 4A

Synthesis of Compound 1

Step 1: Synthesis of Compound 1 (SY-2 or SY-No-dPEG9-OMe)

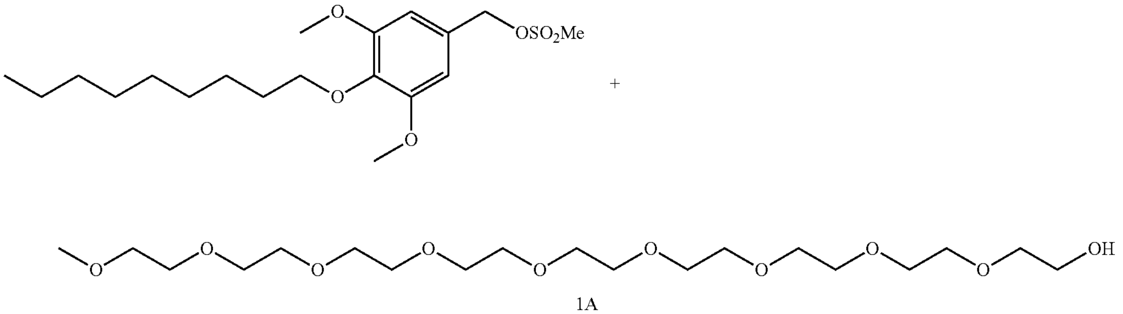

1A

KO$^t$Bu anhydrous THF

-continued

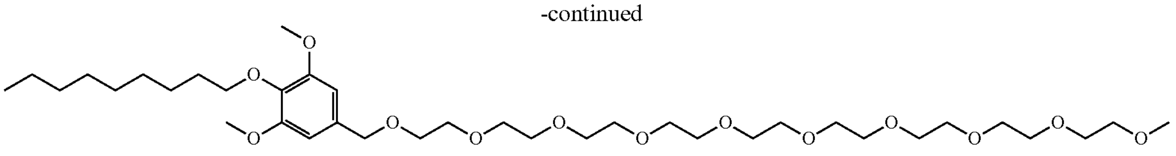

Compound 1 (SY-2)

Starting with compounds 3,5-dimethoxy-4-(nonyloxy) benzyl methanesulfonate and 1A, compound 1 was synthesized using the procedure described in Example 4. The structure was confirmed by $^{1}H$ NMR (400 MHz, $CDCl_3$) δ 6.496 (s, 2H), 4.419 (s, 2H), 3.879-3.844 (t, J=6.9 Hz, 2H), 3.765 (s, 6H), 3.618-3.561 (m, 22H), 3.307 (s, 6H), 1.700-1.629 (m, 3H), 1.535-1.465 (m, 2H), 1.379-1.330 (m, 4H), 1.264-1.186 (m, 12H), 0.822-0.788 (m, 6H).

Example 4B

One or more procedures according to Examples 1~4 were used to prepare other compounds disclosed herein by exposing a suitable starting material to different aliphatic halides and then performing similar conversion steps from the aliphatic-substituted intermediate to the final product (that is, similar conversion steps as outlined in Examples 2-4).

Compound 3 (SY-No-PEG750-OMe or SY-207)

Compound 3 (SY-207) (PEG750)

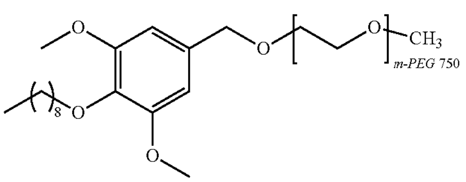

The structure was confirmed by $^{1}H$ NMR (400 MHz, $CDCl_3$) δ 6.579 (s, 2H), 4.503 (s, 2H), 3.851 (m, 2H), 3.788 (s, 6H), 3.657 (m, 103H), 3.466 (s, 3H), 1.451 (m, 2H), 1.284 (m, 12H), 0.891 (m, 3H).

Compound 4 (SY-Oc-dPEG9-OMe)

Compound 4

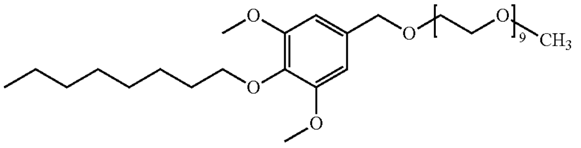

The structure was confirmed by $^{1}H$ NMR (400 MHz, $CDCl_3$) δ 6.457 (s, 2H), 4.377 (s, 2H), 3.835-3.796 (t, J=6.87 Hz, 2H), 3.721 (s, 6H), 3.580-3.504 (m, 22H), 3.259 (s, 3H), 1.657-1.585 (m, 2H), 1.355-1.279 (m, 2H), 1.235-1.147 (m, 12H), 0.779-0.735 (m, 6H).

Compound 5 (SY-Pe-dPEG9-OMe)

Compound 5

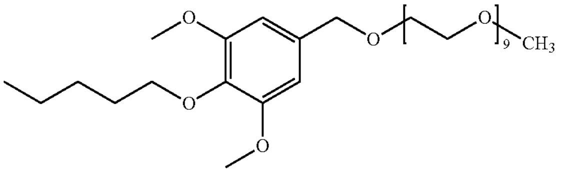

The structure was confirmed by $^{1}H$ NMR (400 MHz, $CDCl_3$) δ 6.448 (s, 2H), 4.361 (s, 2H), 3.825-3.786 (t, J=6.88 Hz, 2H), 3.707 (s, 6H), 3.565-3.509 (m, 22H), 3.249 (s, 3H), 1.654-1.586 (m, 2H), 1.338-1.203 (m, 6H), 0.806-0.761 (t, J=7.17 Hz, 3H).

Compound 6 (SY-iPe-dPEG9-OMe)

Compound 6

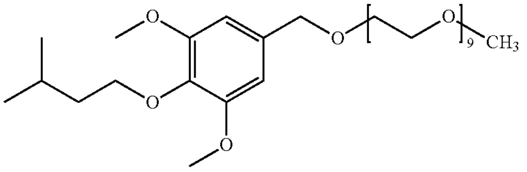

The structure was confirmed by $^{1}H$ NMR (400 MHz, $CDCl_3$) δ 6.403 (s, 2H), 4.324 (s, 2H), 3.811-3.778 (t, J=6.87 Hz, 2H), 3.678 (s, 6H), 3.495-3.460 (m, 36H), 3.387-3.362 (m, 2H), 3.206 (s, 3H), 1.755-1.654 (m, J=13.46 Hz, 1H), 1.498-1.446 (q, J=6.88 Hz, 2H), 0.782-0.762 (d, J=6.66 Hz, 6H).

Compound 7 (SY-DMB-dPEG9-OMe)

Compound 7

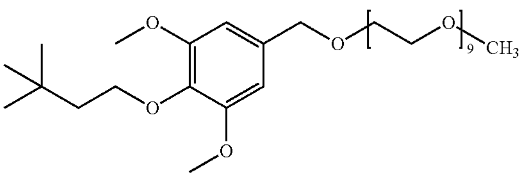

The structure was confirmed by $^{1}H$ NMR (400 MHz, $CDCl_3$) δ 6.441 (s, 2H), 4.358 (s, 2H), 3.886-3.842 (t, J=8.21 Hz, 2H), 3.706 (s, 6H), 3.568-3.490 (m, 22H), 3.242 (s, 3H), 1.633-1.582 (t, J=7.25 Hz, 2H), 0.812 (s, 9H).

Compound 8 (SY-2MP-dPEG9-OMe)

Compound 8

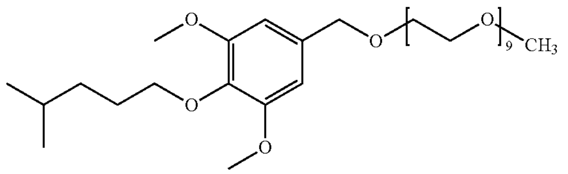

The structure was confirmed by $^1H$ NMR (400 MHz, $CDCl_3$) δ 6.394 (s, 2H), 4.321 (s, 2H), 3.767-3.726 (t, J=7.01 Hz, 2H), 3.671 (s, 6H), 3.517-3.463 (m, 22H), 3.206 (s, 3H), 1.614-1.541 (m, 2H), 1.453-1.373 (m, 1H), 1.176-1.118 (m, 2H), 0.737-0.720 (d, J=6.62 Hz, 6H).

Compound 9 (SY-No-dPEG9-OH)

Compound 9

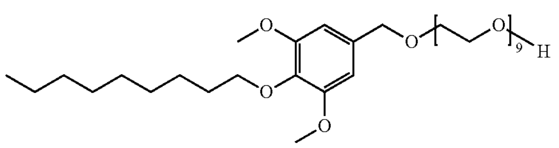

Example 5

Figure 1B:
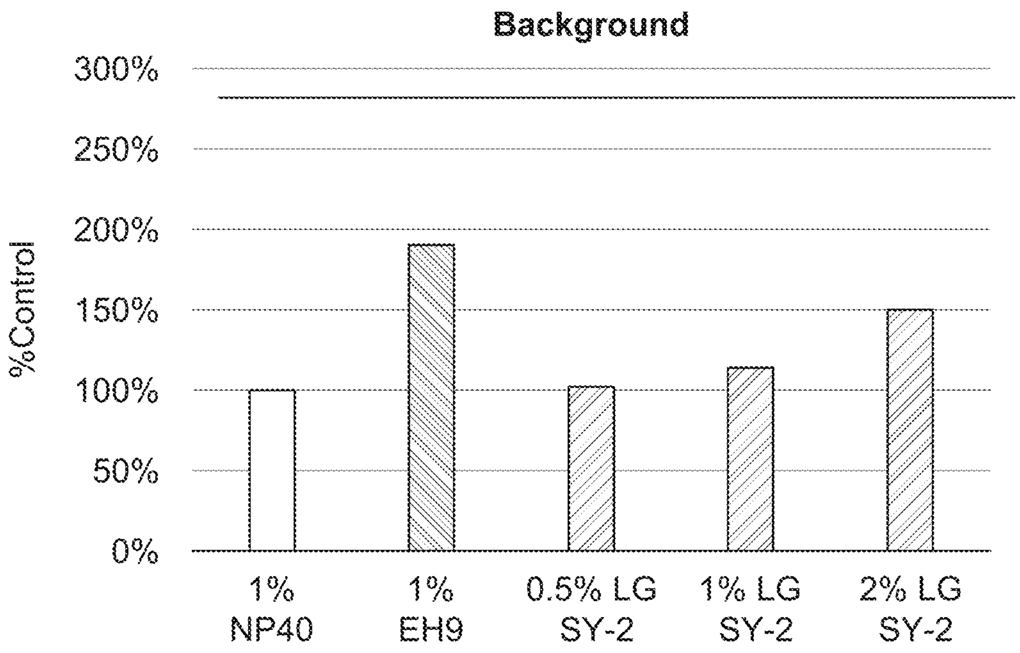
Figure 2:
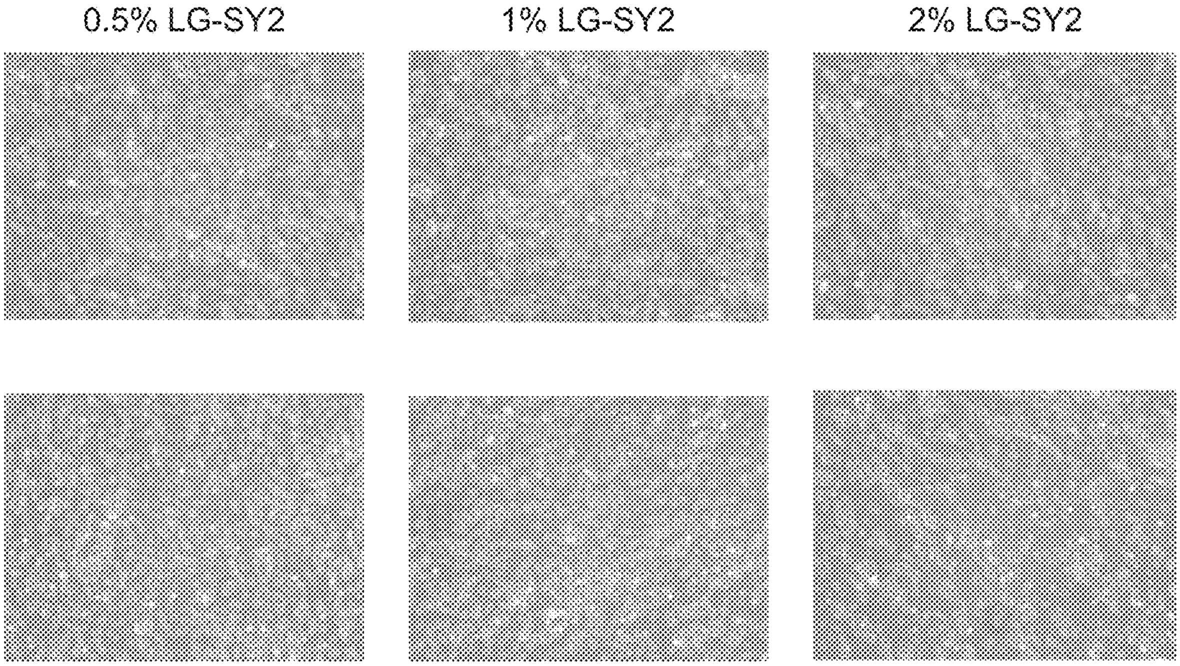
FIG. 2 shows microscopic digital images of the cells after lysing treatment with compound 1 (SY-2), establishing that Compound 1 (SY-2) is sufficiently mild and does not lyse the nucleus.

In this example, the ability to use compounds according to the present disclosure as replacements for the conventional surfactants, Tergitol™ NP-40 (commercially available from Thermo Fisher) and EH9 (commercially available from Dow Inc.), was evaluated. In this example, a compound according to the present disclosure, SY-2 (structure shown below), was used as an IP lysis buffer and used for cell lysing. Similar evaluations were conducted with Tergitol™ NP-40 or EH9 for comparison. The IP lysis buffer recipe was as follows: 25 mM Tris-HCl PH 7.4, 150 mM NaCl, 1 mM EDTA, 1-2% surfactant (either SY-2 at 1%, 1.5%, and 2%; Tergitol™ NP-40 at 1%; or EH9 at 1%), and 5% glycerol. In evaluations using SY-2, the SY-2 compound was resuspended to a 10% solution in $ddH_2O$ and, in some examples, was further diluted to 5%. Cell pellets were resuspended in 0.5 ml buffer and incubated on ice for 15 minutes then centrifuged 17,000×g for 10 minutes. Resulting supernatants were used for BCA (THF #23225) analysis (FIGS. 1A and 1B), with cell/nuclei imaging from resuspended pellets shown in FIG. 2 (10× magnification). FIGS. 1A and 2 show that lysing with Compound 1 (SY-2) shows good protein recovery with no interference and further establishes that nuclei appear normal. FIG. 1B shows results suggesting that the fluorescent probe can produce a higher signal without protein.

Compound 1 (SY-2)

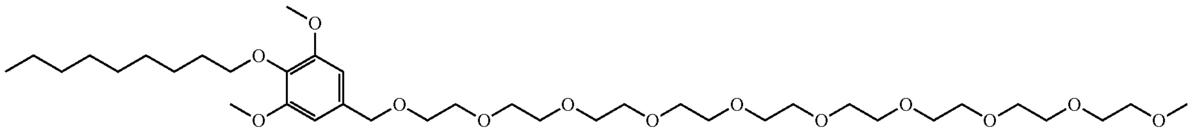

The structure was confirmed by $^1H$ NMR (400 MHz, $CDCl_3$) δ 6.496 (s, 2H), 4.418 (s, 2H), 3.884-3.845 (t, J=6.87 Hz, 2H), 3.764 (s, 6H), 3.598-3.543 (m, 22H), 1.705-1.631 (m, 4H), 1.402-1.320 (m, 4H), 1.269-1.197 (m, 12H), 0.821-0.786 (m, 6H).

Compound 10 (SY-No-dSPEG9-OMe)

Compound 10

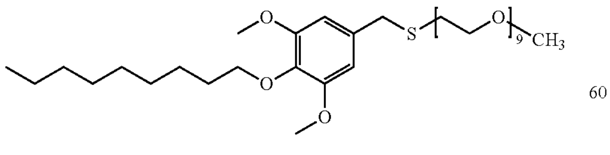

The structure was confirmed by $^1H$ NMR (400 MHz, $CDCl_3$) δ 6.534 (s, 2H), 3.936 (t, 2H), 3.902 (s, 6H), 3.597 (m, 25H), 3.549 (m, 2H), 3.368 (s, 3H), 2.649 (m, 2H), 1.730 (m, 2H), 1.403 (m, 2H), 1.277 (m, 10H), 0.889 (m, 3H).

Example 6

Figure 3:
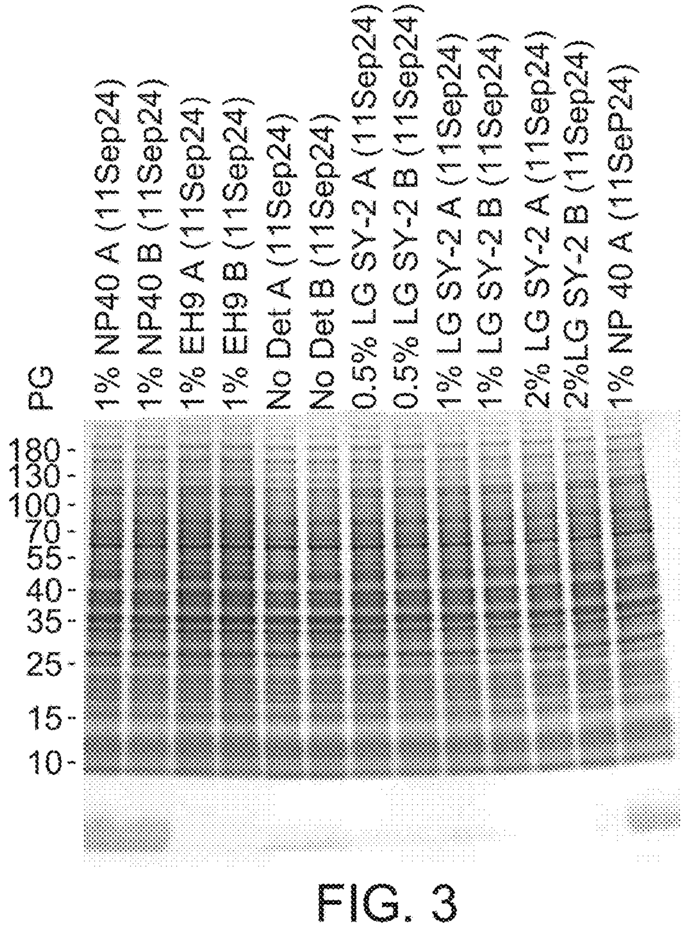
FIG. 3 is a digital image showing a gel after performing SDS-PAGE gel electrophoresis and Coomassie staining on the lysate obtained from using the Compound 1 (SY-2) for cell lysis, and comparing with results obtained from using conventional non-ionic surfactants Tergitol™ NP-40 and EH9.
Figure 4:
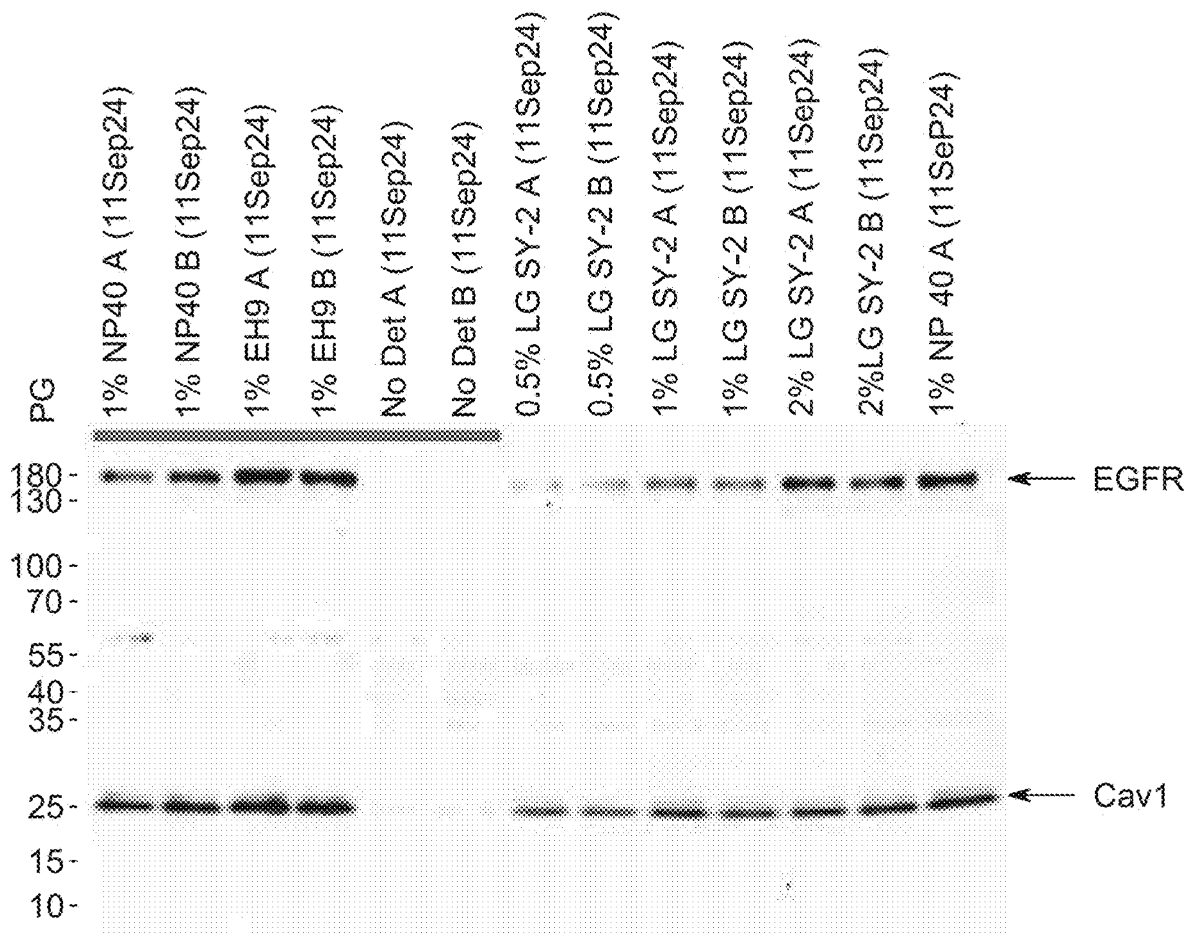
FIG. 4 is a digital image of a nitrocellulose membrane after transferring an SDS-PAGE gel run with the Compound 1 (SY-2), Tergitol™ NP-40, and EH9, and performing detection with EGFR and Cav1, wherein results are shown for the Compound 1 (SY-2), Tergitol™ NP-40, and EH9.
Figure 5:
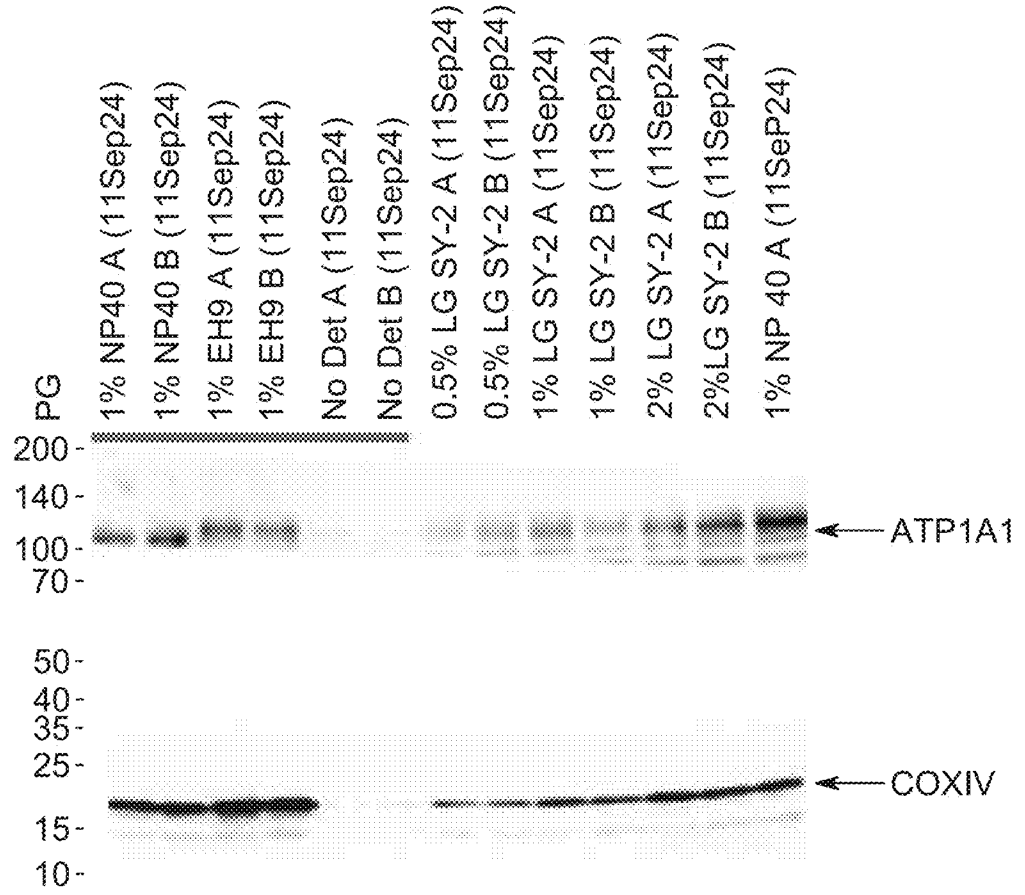
FIG. 5 is a digital image of a nitrocellulose membrane after transferring an SDS-PAGE gel run with the Compound 1 (SY-2), Tergitol™ NP-40, and EH9, and performing detection with ATP1A1 and COXIV, wherein results are shown for the Compound 1 (SY-2), Tergitol™ NP-40, and EH9.

In this example, supernatants from Example 5 were analyzed using SDS-PAGE gel electrophoresis, wherein 10 μg of each sample was run on 4-8% Tris-Glycine midi gels. One gel was stained with Coomassie Stain Gel Code Blue (THF #1860957), which results shown in FIG. 3. Two gels were transferred to nitrocellulose using Power Blotter and detected with (i) EGFR (CST #4267, anti-RB, 1:500) and Cav1 (CST #3238, anti-RB, 1:1,000), results in FIG. 4; and (ii) ATP1A1 (THF #MA3-928, anti-M, 1:2,000); and COXIV (CST #2650, anti-$R^b$, 1:1,000), results in FIG. 5.

The results from this example show that the lysate run on SDS-PAGE looks similar to the controls (i.e., the Tergitol™ NP-40 and EH9 samples) in terms of total protein and membrane protein recovery, thus establishing that compounds of the present disclosure can be used as replacements for conventional surfactants.

Example 7

In Silico Toxicology Predictions

Computational toxicology predictions were performed using a combination of QSAR (Quantitative Structure—

Activity Relationship) and modeling platforms (including ECOSAR (Ecological Structure Activity Relationships) Class Program (Version 2-2), DEREK Nexus (Version 6.4.2), SARAH Nexus (Version 5.0.0), and ToxTree (Version 3.1.0-1851-1525442531402). The models assessed endpoints including: aquatic toxicity (fish, *daphnia*, algae); carcinogenicity; mutagenicity and genotoxicity; skin and eye irritation potential; endocrine disruption and reproductive toxicity alerts.

Comparative analyses were performed between select compounds of the current application, including Compound 1 (SY-No-dPEG9-Ome), Compound 9 (SY-No-dPEG9-OH), and Compound 10 (SY-No-dSPEG9-OMe), with results for Nonidet™ NP-40 (NP-40), and Triton™ X-100 (TX-100). Results were reported as No Alert/Low Concern, Equivocal/Moderate Concern, Positive Alert/High Concern, and Unknown.

TABLE 1 shows the summary results for the in silico testing.

| | NP-40 | TX-100 | SY-No-dPEG9-OMe | SY-No-dPEG9-OH | SY-No-dSPEG9-OMe |
|---|---|---|---|---|---|
| ECOSAR: Aquatic toxicity | Positive Alert/High Concern | Positive Alert/High Concern | No Alert/Low Concern | No Alert/Low Concern | No Alert/Low Concern |
| ToxTree: Sensitization | No Alert/Low Concern | No Alert/Low Concern | No Alert/Low Concern | No Alert/Low Concern | No Alert/Low Concern |
| ToxTree: Eye irritation | Unknown | Unknown | No Alert/Low Concern | No Alert/Low Concern | No Alert/Low Concern |
| ToxTree: Skin irritation | Positive Alert/High Concern | Positive Alert/High Concern | No Alert/Low Concern | No Alert/Low Concern | Unknown |
| ToxTree: Carcinogenicity | No Alert/Low Concern | No Alert/Low Concern | No Alert/Low Concern | No Alert/Low Concern | No Alert/Low Concern |
| ToxTree: Micronucleus | No Alert/Low Concern | No Alert/Low Concern | Positive Alert/High Concern | Positive Alert/High Concern | Positive Alert/High Concern |
| ToxTree: Ames Genotoxicity | No Alert/Low Concern | No Alert/Low Concern | No Alert/Low Concern | No Alert/Low Concern | No Alert/Low Concern |
| Nexus: ICHM7 | No Alert/Low Concern | No Alert/Low Concern | No Alert/Low Concern | No Alert/Low Concern | No Alert/Low Concern |
| Nexus: Sarah | No Alert/Low Concern | No Alert/Low Concern | No Alert/Low Concern | No Alert/Low Concern | No Alert/Low Concern |
| Nexus: Derek (Other Alerts) | Positive Alert/High Concern | Positive Alert/High Concern | Equivocal/Moderate Concern | Equivocal/Moderate Concern | Equivocal/Moderate Concern |
| Nexus: Derek (Mutagenicity) | No Alert/Low Concern | No Alert/Low Concern | No Alert/Low Concern | No Alert/Low Concern | No Alert/Low Concern |

Table 1 shows the results from ECOSAR (aquatic toxicity), ToxTree (sensitization, eye irritation, skin irritation, carcinogenicity, micronucleus, Ames genotoxicty), and NEXUS (ICHM7, Sarah, Derek). Results are reported as No Alert/Low Concern, Equivocal/Moderate Concern, Positive Alert/High Concern, and Unknown.

The in silico results predict that compounds of Formula I have improved toxicological and environmental safety profiles as compared to Triton™ X-100 and Nonidet™ NP-40, particularly with respect to aquatic toxicity. These findings support their potential as safer, more environmentally-friendly, regulatory-compliant substitutes for non-ionic surfactants in life science, industrial, and diagnostic applications.

Example 8

Fish Acute Toxicity Test (OECD 236)

The acute aquatic toxicity of certain compounds disclosed herein on freshwater fish are evaluated under controlled laboratory conditions in accordance with OECD Test Guideline 236 (Fish Embryo Acute Toxicity Test). This study is designed to determine the maximum tolerable dose (MTD) which does not cause overt toxicity, and the concentration that results in 50% lethality (LC50).

To test the acute aquatic toxicity *Danio rerio* (zebrafish) are used as a representative freshwater species. The test system and environmental parameters are maintained as follows: zebrafish embryos are fertilized. At three hours post-fertilization (hpf), one embryo is placed in each well of a pre-conditioned 24-well plates. Liquid is gently aspirated from the wells of the 24-well plate and replaced by 2.0 ml of test solution, consisting of solutions containing compounds of Formula I in varying concentrations (0.1, 0.3, 1, and 3 mg/L (ppm)). Additional wells are similarly prepared using by-products of Compounds of Formula I, TX-100 and NP-40. Plates are sealed and maintained at a temperature of 26 °C Initial assessment of the embryos occurs at 24 hpf when the presence of dead embryos is recorded, observations recorded, and the plates resealed. This is repeated at 24-hour intervals up to 96 hpf. Phenotypical data are entered as 1 or 0 (1=abnormal, 0=normal) for the following: mortality, somites, detachment of the tail-bud from the yolk sac, heartbeat, cardiac edema and hatching. Overt deformities in other areas are noted. $LC_{50}$ values are estimated at 96 hours.

Based on in silico modeling, the 96-hour $LC_{50}$ for compounds of Formula I indicate low acute aquatic toxicity under GHS and REACH classification schemes as compared to Triton™ X-100 and Nonidet™ NP-40.

The results of this study corroborate in silico toxicity predictions, demonstrating that compounds of Formula I present minimal risk to aquatic organisms and may be considered environmentally safer alternatives to Triton™ X-100 and Nonidet™ NP-40.

Example 9

Fish Acute Toxicity Test (*Daphnia magna*)

Comparative acute aquatic toxicity of projected degradation by-products of Formula I was compared to the known degradation by-products Triton™ X-100 and Tergitol™ NP-40. *Daphnia magna* was selected as a representative freshwater invertebrate model organism to assess acute toxicity, using DAPHTOXKIT F test kit by Microbiotests, Inc.

Dormant eggs of *Daphnia magna* were rinsed to remove storage media and transferred to a hatching petri dish in 15 ml pre-aerated standard freshwater. The Petri dish was covered and incubated for 72 h at 20-22 °C to allow the eggs to hatch.

Solutions of the projected by-product of Formula I:

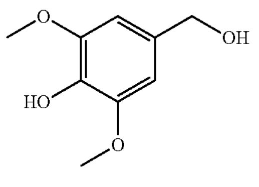

and the known by-products of Triton™ X-100;

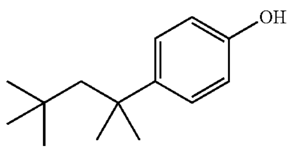

and Tergitol™ NP-40:

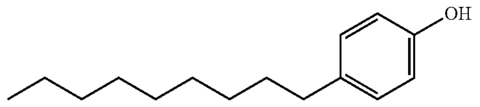 [SMILES: CCCCCCCCCc1ccc(O)cc1]

were prepared in the following manner: each by-product was diluted to 1% in methanol and then diluted to 0.001% in twice distilled H2O, to reach a concentration of 10 mg/L. The solutions were further diluted to 2.0 mgL, 3.0 mg/L and 5.0 mg/L for each by-product. Solutions of 2.0 mgL, 3.0 mg/L and 5.0 mg/L methanol were prepared.

A multiwell plate was labeled and 10 mL saltwater added to a well as control; an additional well was prepared using 10 ml of 2.0 mg/L KCR207. 10 mL of each concentration of methanol or TX-100, NP-40 or Formula I by-product was added into separate wells. Next, 5 *Daphnia* neonates were transferred into each test well. The plate was covered tightly and incubated at 20 °C in darkness. The number of immobilized (including dead) neonates were recorded at 24 h and 48 h, and the percentage immobilized neonates was calculated (Table 2).

TABLE 2

| | 24 HR | 48 HR |
|---|---|---|
| Control | 0% | 5% |
| 2.0 mg/L $K_2Cr_2O_7$ | 100% | 100% |
| 2.0 mg/L Meth | 0% | 0% |
| 3.0 mg/L Meth | 0% | 0% |
| 5.0 mg/L Meth | 0% | 0% |
| 2.0 mg/L Triton ™ X-100 By-product | 5% | 15% |
| 3.0 mg/L Triton ™ X-100 By-product | 45% | 55% |
| 5.0 mg/L Triton ™ X-100 By-product | 95% | 100% |
| 2.0 mg/L Nonidet ™ NP-40 By-product | 15% | 55% |
| 3.0 mg/L Nonidet ™ NP-40 By-product | 100% | 100% |
| 5.0 mg/L Nonidet ™ NP-40 By-product | 100% | 100% |
| 2.0 mg/L Formula I By-product | 5% | 10% |
| 3.0 mg/L Formula I By-product | 0% | 15% |
| 5.0 mg/L Formula I By-product | 0% | 15% |

Table 2 shows *Daphnia* study results with percentage of fish immobilized after 24 and 48 hours in saltwater control, $K_2Cr_2O_7$; methanol at 2.0, 3.0, or 5.0 mg/L; and by-products of Triton™ X-100, Nonidet™ NP-40, or compounds of this disclosure at 2.0, 3.0, and 5.0 mg/L.

Results show that by-products of Formula I showed significantly lower aquatic toxicity than the $K_2Cr_2O_7$ control, Triton™ X-100 by-product, and Nonidet™ NP-40 by-product. Immobilization did not increase significantly with higher doses of Formula I by-product, while significantly higher dose-dependent immobilization was observed with the by-products of Triton™ X-100 and Nonidet™ NP-40. The by-product of Formula I did not reach $EC_{50}$ (the concentration at which 50% of the organisms are immobilized) at 5.0 mg/L. Similar tests are performed on the individual compounds to further demonstrate similar improved toxicity profile. The results of this study demonstrate that compounds of this disclosure are environmentally safer alternatives to Triton™ X-100 and Nonidet™ NP-40.

Example 10

Biodegradability (OECD 301B)

In this example, compounds of this disclosure are tested according to OECD 301B to determine biodegradability. The compounds of this disclosure are tested, and biodegradability results are calculated, according to acceptable test conditions under OECD 301B. A compound is determined to be "readily biodegradable" if it achieves a 60% biodegradability result, which is equivalent to 60% of ThOD (theoretical oxygen demand) or ThCO2 (theoretical carbon dioxide) production within a ten-day window during a 28-day test.

Compounds of this disclosure are anticipated to achieve a higher percentage of biodegradability than either Triton™ X-100 or Nonidet™ NP-40.

In view of the many possible aspects to which the principles of the present disclosure may be applied, it should be recognized that the illustrated aspects are only preferred examples of the disclosure and should not be taken as limiting the scope of the present disclosure. Rather, the scope is defined by the following claims. We therefore claim as our invention all that comes within the scope and spirit of these claims.

We claim:

1. A compound having a structure according to Formula I,

Formula I

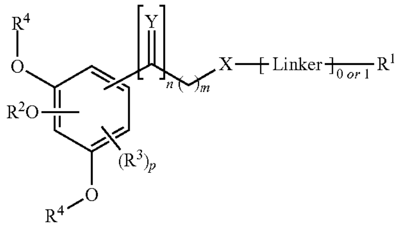

wherein:

$R^1$ is a linear heteroaliphatic group;

$R^2$ is a lipophilic group;

X is oxygen;

$R^3$ is selected from heteroaliphatic, aliphatic, or aryl;

each $R^4$ independently is aliphatic;

Y is selected from oxygen, sulfur, or $N(R^5)$;

the linker, when present, is aliphatic or has a formula —C(═Z)—W—C(═Z)—X', wherein each Z independently is oxygen, sulfur, or $NR^5$, W is an aliphatic or heteroaliphatic group, and X'O is oxygen, sulfur, or $NR^{5-}$;

n is 0;

m is an integer selected from 1 to 6;

p is an integer selected from 0 to 2; and each $R^5$ group independently is selected from hydrogen, aliphatic, aromatic, or heteroaliphatic.

2. The compound of claim 1, wherein $R^3$ independently is —O—$C_{1-6}$alkyl, —O—$C_{3-6}$cycloalkyl,

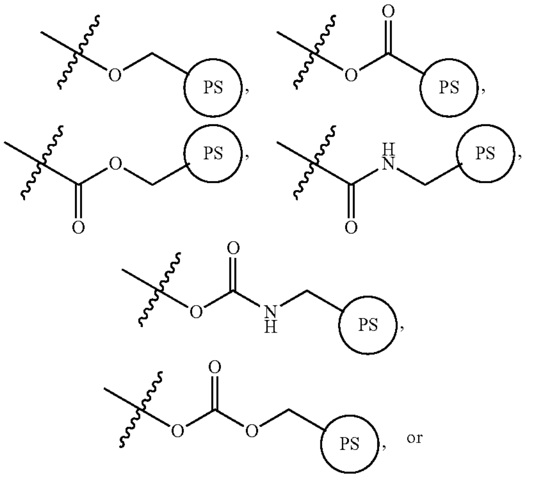

or

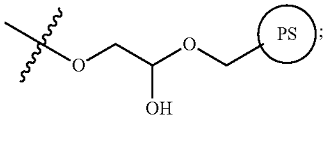

and wherein PS is a polystyrene bead.

3. The compound of claim 1 having a formula according to any one of Formulas IC-IF:

Formula IC

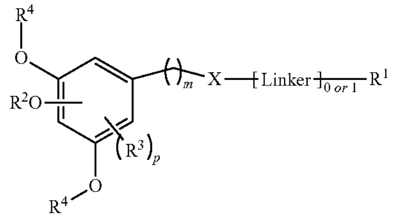

Formula ID

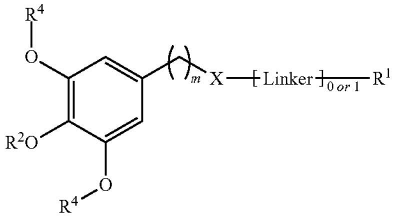

Formula IE

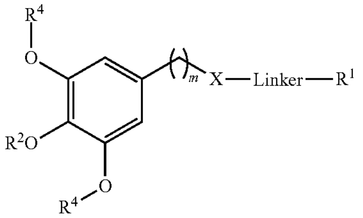

Formula IF

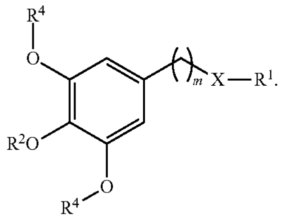

4. The compound of claim 1, wherein the $R^1$ and $R^2$ groups are selected to provide a hydrophilic-lipophilic balance value ranging from 10 to 18.

5. The compound of claim 1, wherein the linear heteroaliphatic group is a polyalkylene oxide.

6. The compound of claim 5, wherein the linear heteroaliphatic group is a PEG group having a mass average molecular weight ranging from 500 g/mol to 800 g/mol.

7. The compound of claim 1, wherein $R^2$ is a $C_{2-25}$alkyl group which is linear, branched, cyclic, or a combination thereof.

8. The compound of claim 1, wherein each $R^4$ independently is a methyl, ethyl or $C_{3-10}$alkyl group.

9. The compound of claim 1, wherein the linker is present and is a $C_{1-25}$aliphatic group.

10. The compound of claim 1, wherein the linker is present and is $-(CH_2)_q-$, $-C(=O)(CH_2)_qC(=O)-O-$, or $-C(=S)(CH_2)_qC(=S)-O-$, $-C(=O)N(H)(CH_2)_qN(H)C(=O)-O-$, wherein each q independently is an integer ranging from 1 to 10.

11. The compound of claim 1 having a structure according to Formulas IG or IH:

Formula IG

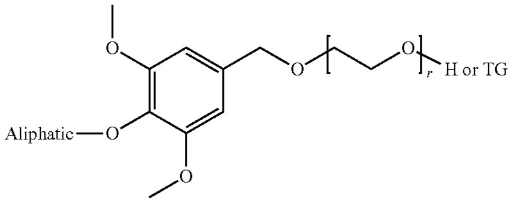

Formula IH

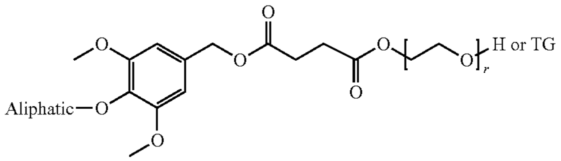

wherein the aliphatic group is linear, branched, or cyclic, or a combination thereof; TG, if present, is a terminating group that is an aliphatic group; and r is an integer selected from 2 to 20.

12. The compound of claim 11, wherein the aliphatic group is a linear $C_{2-20}$alkyl group; a branched $C_{2-20}$alkyl group; a cyclic $C_{3-20}$alkyl group; or a combination of any such linear, branched, and/or cyclic groups.

13. The compound of claim 12, wherein the aliphatic group is isopentyl, 2-methylpentyl, heptyl, 2,2-dimethylbutyl, pentyl, octyl, or nonyl.

14. The compound of claim 11, wherein the TG group is a methyl or $C_{2-10}$alkyl group.

15. A compound having the structure selected from:

1

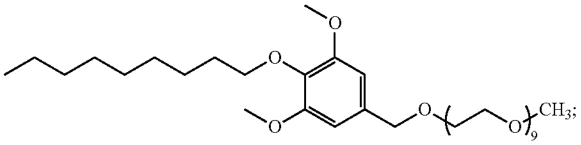

4

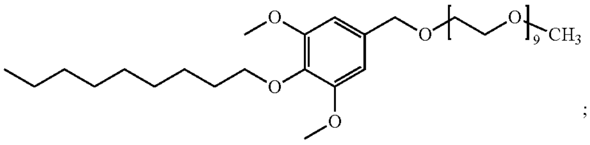

;

5

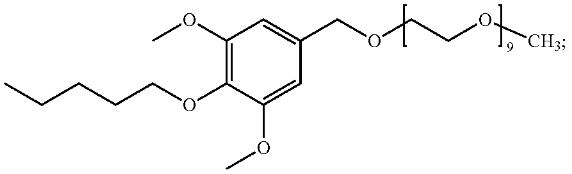

6

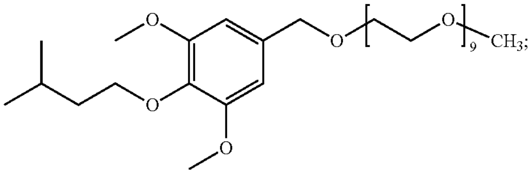

7

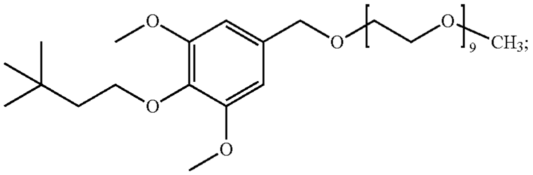

8

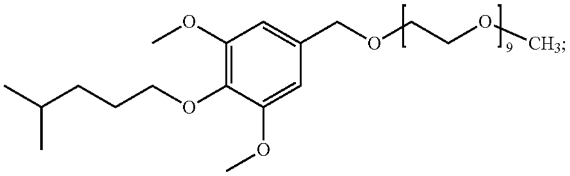

9

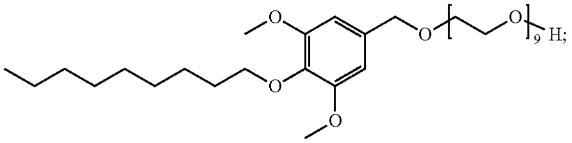

11

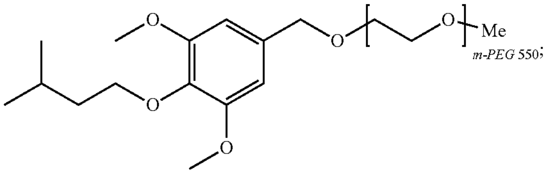

12

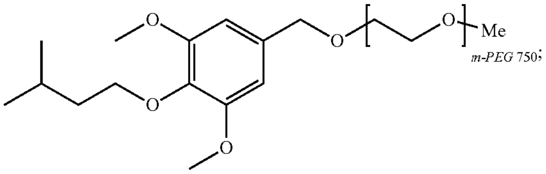

-continued
13
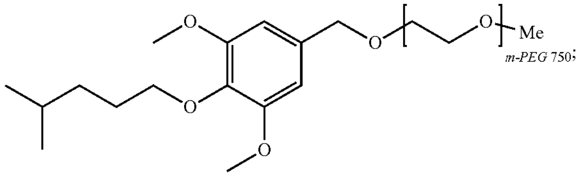
14
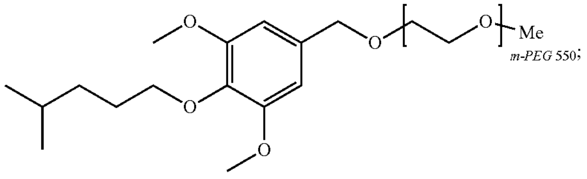
15
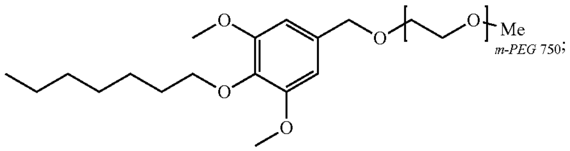
16
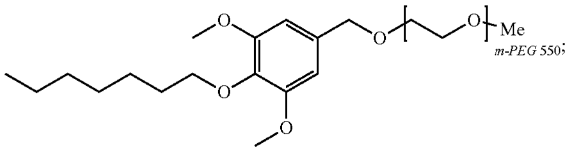
17
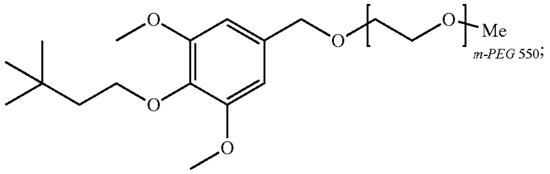
18
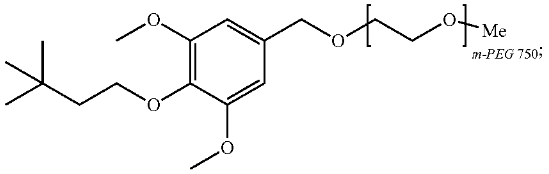
19
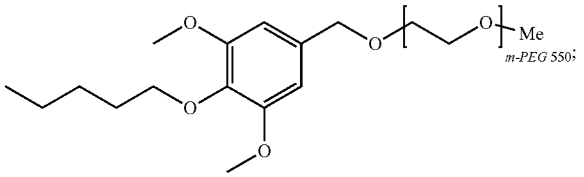
20
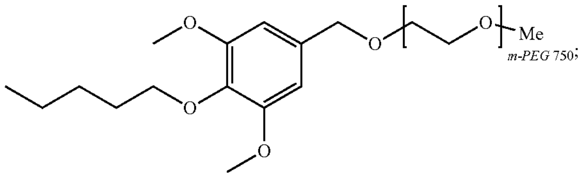
3
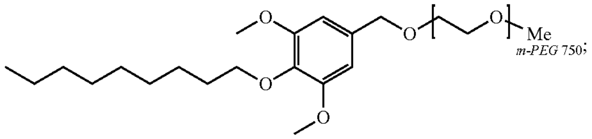
2
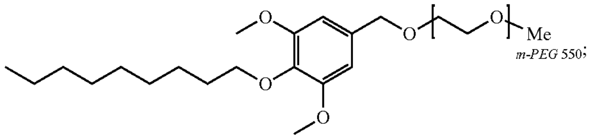
21
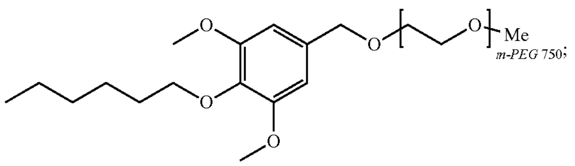
22
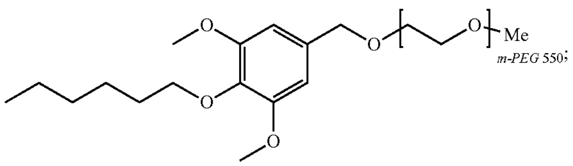
23
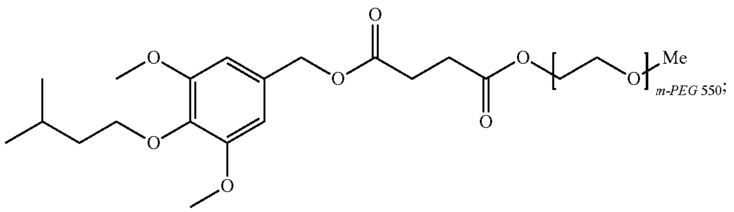
24
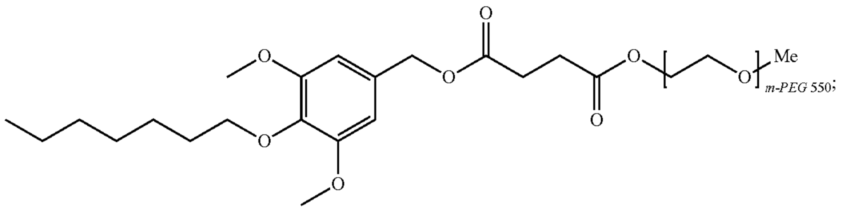

-continued
25
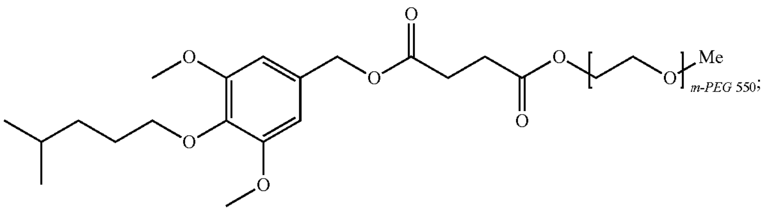
26
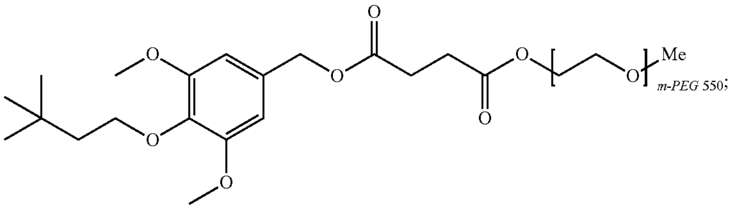
27
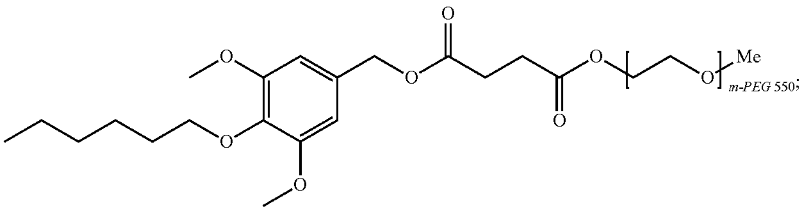
28
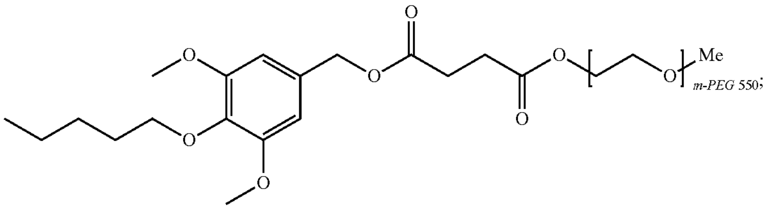
29
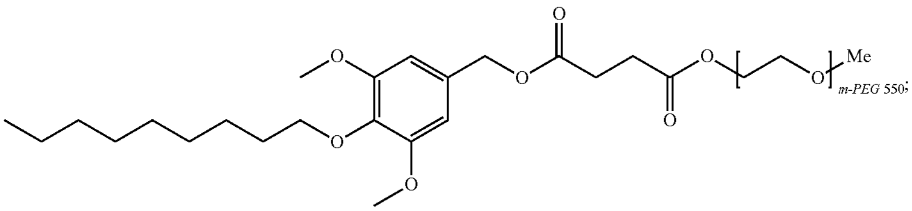
30
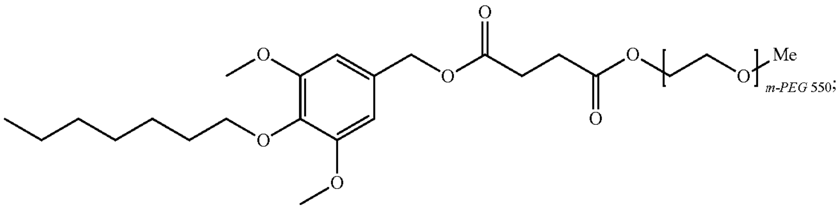
31
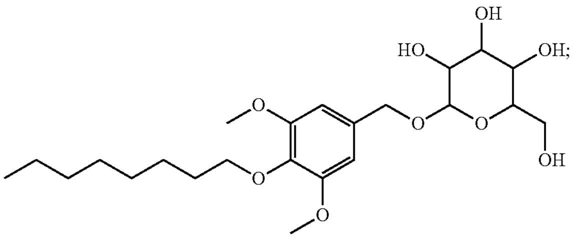

-continued
33
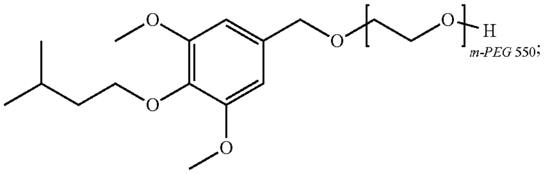
34
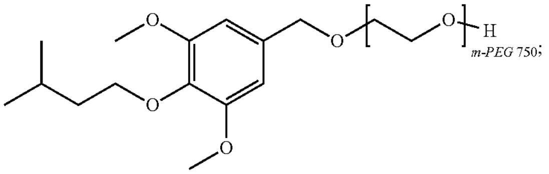
35
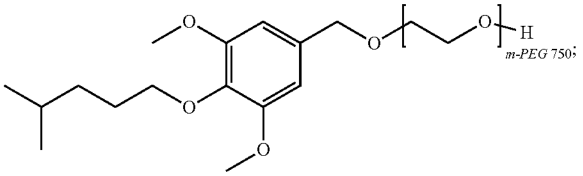
36
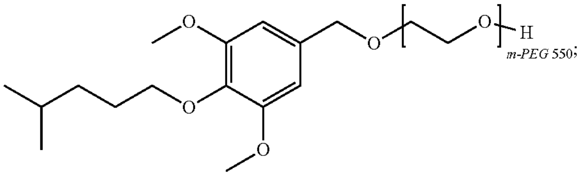
37
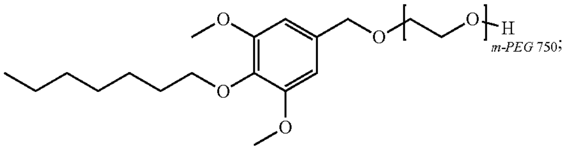
38
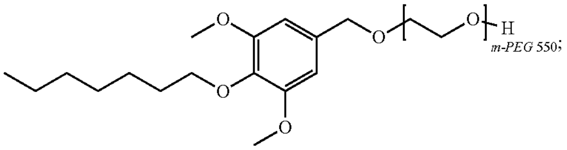
39
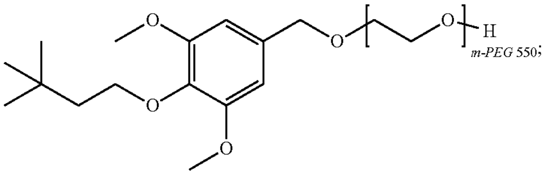
40
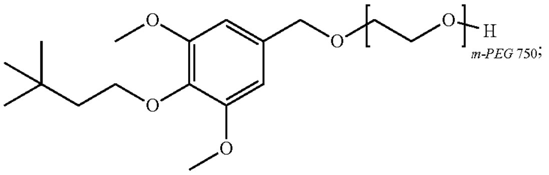
41
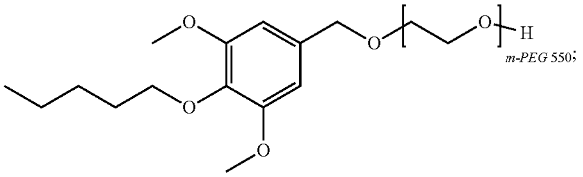
42
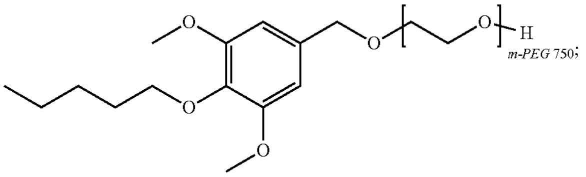
43
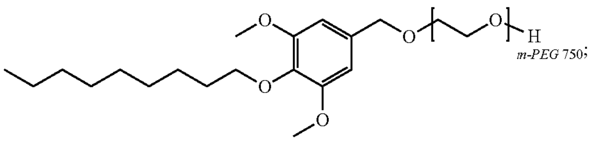
44
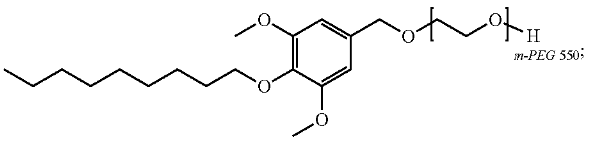
45
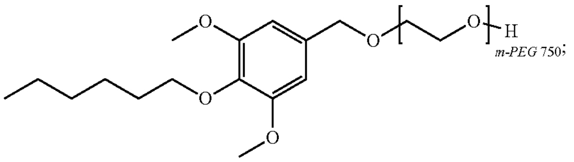
46
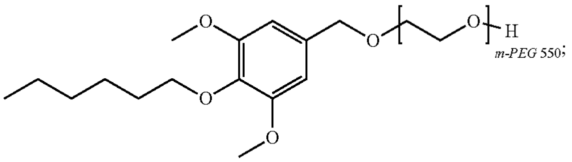
47
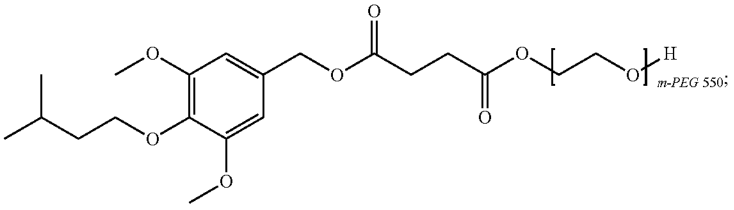

-continued
48
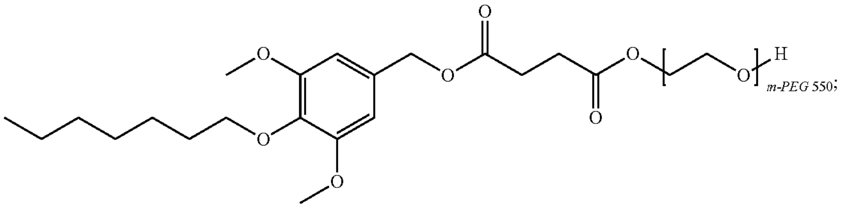
49
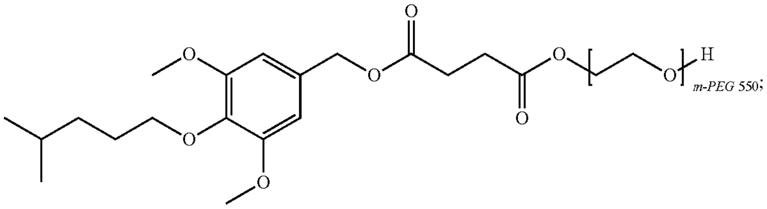
50
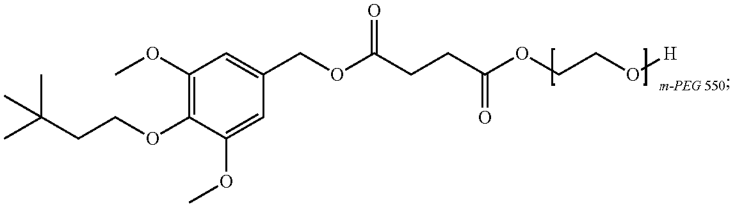
51
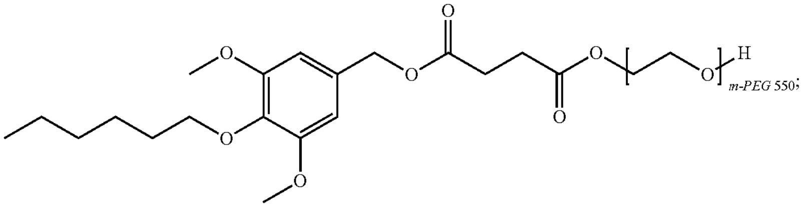
52
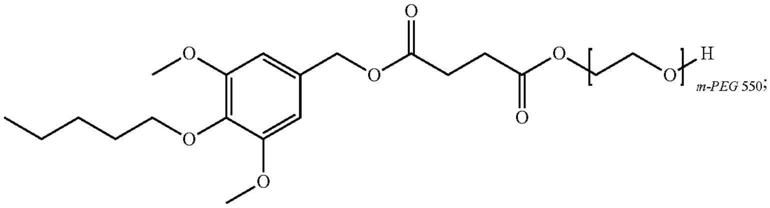
53
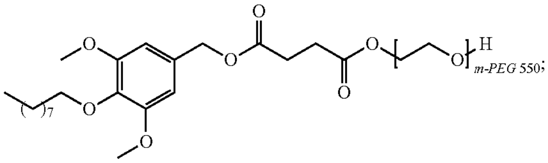
or
54
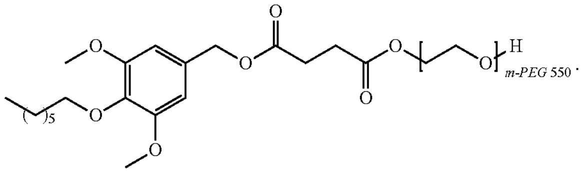
16. A composition, comprising a compound according to claim 1.
* * * * *